(12) United States Patent
Hoffmann et al.

(10) Patent No.: US 12,638,450 B2
(45) Date of Patent: May 26, 2026

(54) OVARIAN CANCER BIOMARKER DETECTION THROUGH OVARIAN BLOOD SAMPLING

(71) Applicant: University of South Australia, Adelaide (AU)

(72) Inventors: Peter Hoffmann, Largs North (AU); Martin K. Oehler, St. Georges (AU)

( * ) Notice: Subject to any disclaimer, the term of this patent is extended or adjusted under 35 U.S.C. 154(b) by 956 days.

(21) Appl. No.: 17/787,868

(22) PCT Filed: Dec. 18, 2020

(86) PCT No.: PCT/AU2020/051400
§ 371 (c)(1),
(2) Date: Jun. 21, 2022

(87) PCT Pub. No.: WO2021/119759
PCT Pub. Date: Jun. 24, 2021

(65) Prior Publication Data
US 2024/0060981 A1 Feb. 22, 2024

(30) Foreign Application Priority Data
Dec. 20, 2019 (AU) ................................. 2019904854

(51) Int. Cl.
| | |
|---|---|
| *G01N 31/00* | (2006.01) |
| *A61K 49/00* | (2006.01) |
| *A61P 35/00* | (2006.01) |
| *G01N 33/50* | (2006.01) |
| *G01N 33/53* | (2006.01) |
| *G01N 33/575* | (2026.01) |
| *G01N 33/57545* | (2026.01) |
| *G01N 33/68* | (2006.01) |
| *G01N 30/72* | (2006.01) |

(52) U.S. Cl.
CPC ... *G01N 33/57545* (2026.01); *A61K 49/0004* (2013.01); *A61P 35/00* (2018.01); *G01N 33/5011* (2013.01); *G01N 33/57585* (2026.01); *G01N 33/6848* (2013.01); *G01N 30/7233* (2013.01)

(58) Field of Classification Search
None
See application file for complete search history.

(56) References Cited

PUBLICATIONS

Imai T, et al., (Elevated expression of E-cadherin and alpha-, beta-, and gamma-catenins in metastatic lesions compared with primary epithelial ovarian carcinomas, Hum Pathol., 2004, vol. 35, pp. 1469-1476) (Year: 2004).*

Weiland ef al., "Ovarian Blood Sampling Identifies Junction Plakoglobin as a Novel Biomarker of Early Ovarian Cancer," Front Oncol 10:1767, 2020. (Year: 2020).*

Tockman et al. (Cancer Research 52:2711s-2718s, 1992) (Year: 1992).*

Tascilar et al. (Annals of Oncology 10,Suppl. 4:S107-S110, 1999) (Year: 1999).*

Imai et al., "Elevated Expression of E-Cadherin and α-, β-, and γ-Catenins in Metastatic Lesions Compared with Primary Epithelial Ovarian Carcinomas," *Hum Pathol* 35:1469-1476, 2004.

International Search Report and Written Opinion, PCT/AU2020/051400, dated Feb. 19, 2021 (14 pages).

Pan et al., "Quantitative Proteomics Analysis Integrated with Microarray Data Reveals That Extracellular Matrix Proteins, Catenins, and P53 Binding Protein 1 Are Important for Chemotherapy Response in Ovarian Cancers," *OMICS* 13:345-354, 2009.

Timms et al., "Discovery of serum biomarkers of ovarian cancer using complementary proteomic profiling strategies," *Proteomics Clin Appl* 8:982-993, 2014.

Voutilainen et al., "Prognostic significance of E-cadherin-catenin complex in epithelial ovarian cancer," *J Clin Pathol* 59:460-467, 2006.

Weiland et al., "Ovarian Blood Sampling Identifies Junction Plakoglobin as a Novel Biomarker of Early Ovarian Cancer," *Front Oncol* 10:1767, 2020.

* cited by examiner

*Primary Examiner* — Lisa V Cook
(74) *Attorney, Agent, or Firm* — Klarquist Sparkman, LLP

(57) ABSTRACT

The present invention is directed to a biological marker of ovarian cancer, including early stage ovarian cancer. Specifically, the present invention provides methods for detecting ovarian cancer in a subject which include detecting an expression level of the biological marker junction plakoglobin in blood of the subject. An expression level of junction plakoglobin that is higher than a reference expression level for junction plakoglobin indicates that the subject has ovarian cancer. Methods of identifying a subject having ovarian cancer and methods of determining if a subject is susceptible to developing ovarian cancer are also provided based on detecting the expression level of junction plakoglobin in blood of the subject. The present invention also extends to methods of treatment of ovarian cancer together with methods of screening a candidate therapeutic agent for use in treating ovarian cancer. Furthermore, compositions and kits for detecting ovarian cancer in a subject are provided, as well as a method of identifying a biomarker for a cancer, including ovarian cancer.

19 Claims, 8 Drawing Sheets

Specification includes a Sequence Listing.

Images after warping with RAIN – not contrast adjusted

Images after warping with RAIN – not contrast adjusted

OVARIAN CANCER BIOMARKER DETECTION THROUGH OVARIAN BLOOD SAMPLING

PRIORITY CLAIM

This application claims priority from Australian provisional patent application number 2019904854 filed on 20 Dec. 2019, the contents of which are to be taken as incorporated herein by this reference.

FIELD OF THE INVENTION

The present invention relates to the identification of a biological marker of ovarian cancer, including early stage ovarian cancer. Specifically, an association between ovarian cancer and an increased expression of junction plakoglobin in blood has been identified. Accordingly, junction plakoglobin is a biomarker that can be utilised for a range of purposes including methods for detecting ovarian cancer in a subject, methods for identifying a subject having ovarian cancer, and methods for determining if a subject is susceptible to developing ovarian cancer. The present invention also relates to methods which can be used to identify biomarkers associated with cancer, including ovarian cancer.

BACKGROUND OF THE INVENTION

Ovarian cancer is one of the leading causes of death from gynaecological malignancies, and accounts for an estimated 239,000 new cases and 152,000 deaths worldwide each year. However, despite advances in surgery and chemotherapies, no substantial improvement in ovarian cancer survival has been observed over the last two decades.

The most widely recognised risk factors for ovarian cancer are menstrual, reproductive and hormonal factors. However, a number of other factors have also been linked to the development of ovarian cancer and these include diet, adult height, weight, and smoking. Furthermore, there have been clinical observations suggesting a genetic component to ovarian cancer risk due to familial aggregations of ovarian cancer. Indeed, women carrying BRCA1 and BRCA2 mutations have been seen to be at higher risk of developing ovarian cancer.

The high mortality rate of ovarian cancer arises due to the asymptomatic progression of the disease resulting in over 70% of cases being diagnosed in advanced stages (International Federation of Gynecology and Obstetrics (FIGO) stage III and IV) when the cancer has spread to the abdominal cavity or to other organs. Detection of ovarian cancer at an early stage, i.e. when it is still confined to the ovary (FIGO stage I), is associated with a 5-year survival rate of over 90% compared to less than 30% for women presenting with advanced ovarian disease (FIGO stage III/IV). Therefore, the detection of ovarian cancer at an early stage is the most effective way to improve overall survival from the disease. However, at present there are no reliable clinically applicable tests and biological markers available for the early detection of ovarian cancer, and so population screening is therefore not possible.

Although cancer antigen 125 (CA125) and HE4 are two protein-based biomarkers that have been clinically approved to distinguish benign from malignant ovarian lesions, to measure disease burden, and to evaluate ovarian cancer treatment, these markers are not elevated in all patients with ovarian cancer and may be increased in healthy women or women with benign diseases. Consequently, they do not have sufficient sensitivity and specificity for population-based risk assessment or early detection. For example, serum levels of CA125 greater than 35 U/mL in women presenting with an adnexal mass is the current gold standard for cancer diagnosis. However, elevated levels of CA125 are only observed in less than 50% of early stage patients and 70% of advanced stage patients. Consequently, CA125 is not a useful tumour marker alone for screening and early detection of ovarian cancer. The main utility of CA125 is for the differential diagnosis of ovarian masses and in cancer follow up.

There are several profound obstacles associated with traditional biomarker discovery focused on tumour-associated antigens. For example, there are quantitative challenges in early-stage disease when the tumour is very small and therefore only very small quantities of the target antigen are produced and released into the blood (which might remain undetectable with currently available technology). There are also qualitative challenges as the markers in many cases are incidental to the disease process, and are often masked by the complexity of the examined biospecimens and presence of high abundant proteins. The problem is further compounded by the genetic diversity of human populations and the influence of uncontrollable environmental factors meaning that potential biomarkers can be overshadowed by the high degree of natural variation in biomarker expression. Finally, obtaining a significant number of human samples of early-stage ovarian cancer for research is difficult due to the rarity of the disease diagnosed at this stage.

Given the lack of early detection tests and limitations of current approaches, there is an urgent need to identify new biomarkers for early stage ovarian cancer, and to develop new methods to identify such biomarkers.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

SUMMARY OF THE INVENTION

The present invention is predicated, in part, on the determination that junction plakoglobin is secreted by malignant ovarian tumours, with the level of junction plakoglobin being higher in blood from ovarian tumours when compared to peripheral blood from patients with the disease. Furthermore, the inventors have found that expression of junction plakoglobin is higher in blood of subjects with ovarian cancer (including early stage ovarian cancer) compared to expression of junction plakoglobin in blood of normal subjects or subjects with benign ovarian tumours. Junction plakoglobin is therefore a new biomarker of ovarian cancer.

Accordingly, in a first aspect the present invention provides a method of detecting ovarian cancer in a subject, the method comprising:

(a) detecting an expression level of junction plakoglobin in blood of the subject;

(b) comparing the expression level of junction plakoglobin in the blood of the subject with a reference expression level for junction plakoglobin; and (c) detecting ovarian cancer in the subject on the basis of the comparison, wherein an expression level of junction plakoglobin in the blood of the subject that is higher than the reference expression level for junction plakoglobin indicates that the subject has ovarian cancer.

In a second aspect, the present invention provides a method of identifying a subject having ovarian cancer, the method comprising:

(a) detecting an expression level of junction plakoglobin in blood of the subject;

(b) comparing the expression level of junction plakoglobin in the blood of the subject with a reference expression level for junction plakoglobin; and (c) identifying the subject as a subject having ovarian cancer on the basis of the comparison, wherein an expression level of junction plakoglobin in the blood of the subject that is higher than the reference expression level for junction plakoglobin indicates that the subject has ovarian cancer.

In a third aspect, the present invention provides a method of determining if a subject is susceptible to developing ovarian cancer, the method comprising:

(a) detecting an expression level of junction plakoglobin in blood of the subject;

(b) comparing the expression level of junction plakoglobin in the blood of the subject with a reference expression level for junction plakoglobin; and (c) determining if the subject is susceptible to developing ovarian cancer on the basis of the comparison, wherein an expression level of junction plakoglobin in the blood of the subject that is higher than the reference expression level for junction plakoglobin indicates that the subject is susceptible to developing ovarian cancer.

In some embodiments of the first to third aspects of the invention, the method is conducted in vitro. Accordingly, in some embodiments, the expression level of junction plakoglobin is detected in a blood sample obtained from the subject. In some embodiments, the blood sample is a serum sample or plasma sample. In some embodiments, serum sample or plasma sample is obtained from peripheral blood of the subject.

In some embodiments of the first to third aspects of the invention, the expression level of junction plakoglobin protein is detected. In some embodiments, the expression level of junction plakoglobin protein is detected using an antibody specific for the junction plakoglobin protein.

In some embodiments of the first to third aspects of the invention, the ovarian cancer is ovarian epithelial carcinoma. In some embodiments, the ovarian epithelial carcinoma is serous ovarian carcinoma, endometrioid ovarian carcinoma, mucinous ovarian carcinoma, or clear cell ovarian carcinoma.

In some embodiments of the first and second aspects of the invention, the ovarian cancer is early stage ovarian cancer. In some embodiments, the early stage ovarian cancer is Stage I ovarian cancer.

In some embodiments of the first and second aspects of the invention, the method further comprises treating a subject in which ovarian cancer has been detected. In some embodiments, treating the subject comprises one or more of removal of one or both ovaries of the subject, chemotherapy, or radiotherapy.

In a fourth aspect, the present invention provides a method of treating ovarian cancer in a subject, comprising:

(a) identifying the subject as a subject with ovarian cancer on the basis that an expression level of junction plakoglobin in blood of the subject is higher than a reference expression level for junction plakoglobin; and (b) treating ovarian cancer in the subject.

In a fifth aspect, the present invention provides a method of treating ovarian cancer in a subject, comprising:

(a) detecting an expression level of junction plakoglobin in blood of the subject;

(b) comparing the expression level of junction plakoglobin in the blood of the subject with a reference expression level for junction plakoglobin;

(c) detecting ovarian cancer in the subject on the basis of the comparison, wherein an expression level of junction plakoglobin in the blood of the subject that is higher than the reference expression level for junction plakoglobin is indicative of ovarian cancer in the subject; and (d) treating ovarian cancer in the subject.

In some embodiments of the fourth and fifth aspects of the invention, treating ovarian cancer in the subject comprises one or more of removal of one or both ovaries of the subject, chemotherapy, or radiotherapy.

In some embodiments of the fourth and fifth aspects of the invention, the expression level of junction plakoglobin has been detected in a blood sample obtained from the subject. In some embodiments, the blood sample is a serum sample or plasma sample. In some embodiments, the serum sample or plasma sample is obtained from peripheral blood of the subject.

In some embodiments of the fourth and fifth aspects of the invention, the expression level of junction plakoglobin protein has been detected, or is, detected. In some embodiments, the expression level of junction plakoglobin protein has been detected using an antibody specific for the junction plakoglobin protein.

In some embodiments of the fourth and fifth aspects of the invention, the ovarian cancer is ovarian epithelial carcinoma. In some embodiments, the ovarian epithelial carcinoma is serous ovarian carcinoma, endometrioid ovarian carcinoma, mucinous ovarian carcinoma, or clear cell ovarian carcinoma. In some embodiments, the ovarian cancer is early stage ovarian cancer. In some embodiments, the early stage ovarian cancer is Stage I ovarian cancer.

In a sixth aspect, the present invention provides a method of screening a candidate therapeutic agent for use in treating ovarian cancer in a subject, wherein the method comprises the step of assaying the candidate therapeutic agent for activity in decreasing the expression level and/or activity of junction plakoglobin in the subject.

In some embodiments of the sixth aspect of the invention, the method comprises:

(a) administering the candidate therapeutic agent to the subject;

(b) detecting the expression level of junction plakoglobin in blood of the subject; and (c) comparing the expression level of junction plakoglobin in the blood of the subject with the expression level of junction plakoglobin in blood of an untreated subject having ovarian cancer, wherein if the expression level of junction plakoglobin in the blood of the subject is lower than the expression level of junction plakoglobin in the untreated subject, the candidate therapeutic agent is useful for treating ovarian cancer.

In some embodiments of the sixth aspect of the invention, the method comprises:

(a) detecting the expression level of junction plakoglobin in blood of a subject who has been administered the candidate therapeutic agent; and (b) comparing the expression level of junction plakoglobin in the blood of the subject with the expression level of junction plakoglobin in blood of an untreated subject having ovarian cancer, wherein if the expression level of junction plakoglobin in the blood of the subject is lower than the expression level of junction plakoglobin in the untreated subject, the candidate therapeutic agent is useful for treating ovarian cancer.

In some embodiments of the sixth aspect of the invention, the expression level of junction plakoglobin is detected in a blood sample obtained from the subject. In some embodiments, the blood sample is a serum sample or plasma sample. In some embodiments, the serum sample or plasma sample is obtained from peripheral blood of the subject.

In some embodiments of the sixth aspect of the invention, the expression level of junction plakoglobin protein is detected. In some embodiments, the expression level of junction plakoglobin protein is detected using an antibody specific for the junction plakoglobin protein.

In some embodiments of the sixth aspect of the invention, the ovarian cancer is ovarian epithelial carcinoma. In some embodiments, the ovarian epithelial carcinoma is serous ovarian carcinoma, endometrioid ovarian carcinoma, mucinous ovarian carcinoma, or clear cell ovarian carcinoma. In some embodiments, the ovarian cancer is early stage ovarian cancer. In some embodiments, the early stage ovarian cancer is Stage I ovarian cancer.

In a seventh aspect, the present invention provides a method of screening a candidate therapeutic agent for use in treating ovarian cancer in a subject, wherein the method comprises:

(a) exposing the candidate therapeutic agent to a cell expressing junction plakoglobin;

(b) measuring for a change in the expression level of junction plakoglobin in the cell; and (c) comparing the expression level of junction plakoglobin in the cell to a reference expression level for junction plakoglobin, wherein if the expression level of junction plakoglobin in the cell is lower than the reference expression level for junction plakoglobin, the candidate therapeutic agent is useful for treating ovarian cancer in a subject.

In some embodiments of the seventh aspect of the invention, the expression level of junction plakoglobin protein is detected. In some embodiments, the expression level of junction plakoglobin protein is detected using an antibody specific for the junction plakoglobin protein.

In some embodiments of the seventh aspect of the invention, the ovarian cancer is ovarian epithelial carcinoma. In some embodiments, the ovarian epithelial carcinoma is serous ovarian carcinoma, endometrioid ovarian carcinoma, mucinous ovarian carcinoma, or clear cell ovarian carcinoma. In some embodiments, the ovarian cancer is early stage ovarian cancer. In some embodiments, the early stage ovarian cancer is Stage I ovarian cancer.

In an eighth aspect, the present invention provides a composition for detecting ovarian cancer in a subject, for identifying a subject having ovarian cancer, or for determining if a subject is susceptible to developing ovarian cancer, the composition including an agent that binds to, or interacts with, junction plakoglobin present in blood of the subject.

In some embodiments of the eighth aspect of the invention, the agent is an antibody specific for junction plakoglobin protein.

In a ninth aspect, the present invention provides a kit for detecting ovarian cancer in a subject, for identifying a subject having ovarian cancer, or for determining if a subject is susceptible to developing ovarian cancer, the kit including means for detecting an expression level of junction plakoglobin in blood of the subject.

In some embodiments of the ninth aspect of the invention, the kit includes an agent that binds to, or interacts with, junction plakoglobin present in blood of the subject. In some embodiments, the agent is an antibody specific for junction plakoglobin protein.

In a tenth aspect, the present invention provides a biomarker of ovarian cancer, the biomarker being junction plakoglobin. In some embodiments, an expression level of junction plakoglobin in the blood of a subject that is higher than a reference expression level for junction plakoglobin is indicative of ovarian cancer in the subject.

In an eleventh aspect, the present invention provides a method of identifying a biomarker for a cancer, the method comprising:

(a) obtaining a blood sample from a subject having the cancer, wherein the blood sample is obtained from venous or arterial blood associated with a malignant tumour;

(b) extracting the protein component of the blood sample;

(c) determining the level of expression of proteins present in the protein component of the blood sample; and (d) identifying a protein present in the protein component of the blood sample that has an expression level higher or lower than a reference expression level for the protein, wherein a protein present in the protein component of the blood sample that has an expression level higher or lower than a reference expression level for the protein is a biomarker for the cancer.

In some embodiments of the eleventh aspect of the invention, after the protein component of the blood sample has been extracted, abundant proteins in the protein component are depleted. In some embodiments, the abundant proteins are depleted by immunoaffinity depletion.

In some embodiments of the eleventh aspect of the invention, the level of expression of proteins present in the protein component of the blood sample is determined by two-dimensional difference gel electrophoresis. In some embodiments, the two-dimensional difference gel electrophoresis is saturation labelling two-dimensional difference gel electrophoresis.

In some embodiments of the eleventh aspect of the invention, a protein present in the protein component of the blood sample that has an expression level higher or lower than a reference expression level for the protein is identified by mass spectrometry. In some embodiments, the mass spectrometry is liquid chromatography tandem mass spectrometry.

In some embodiments of the eleventh aspect of the invention, the reference expression level for the protein is determined from a peripheral blood sample obtained from the subject having the cancer. In some embodiments, the blood sample obtained from the subject is a serum sample or plasma sample.

In some embodiments of the eleventh aspect of the invention, the cancer is ovarian cancer. In some embodiments, the blood sample is an ovarian blood sample. In some embodiments, the ovarian blood sample is obtained from ovarian venous or arterial blood.

BRIEF DESCRIPTION OF THE FIGURES

For a further understanding of the aspects and advantages of the present invention, reference should be made to the following detailed description, taken in conjunction with the accompanying figures which illustrate certain embodiments of the present invention.

DETAILED DESCRIPTION OF THE INVENTION

Figure 1:
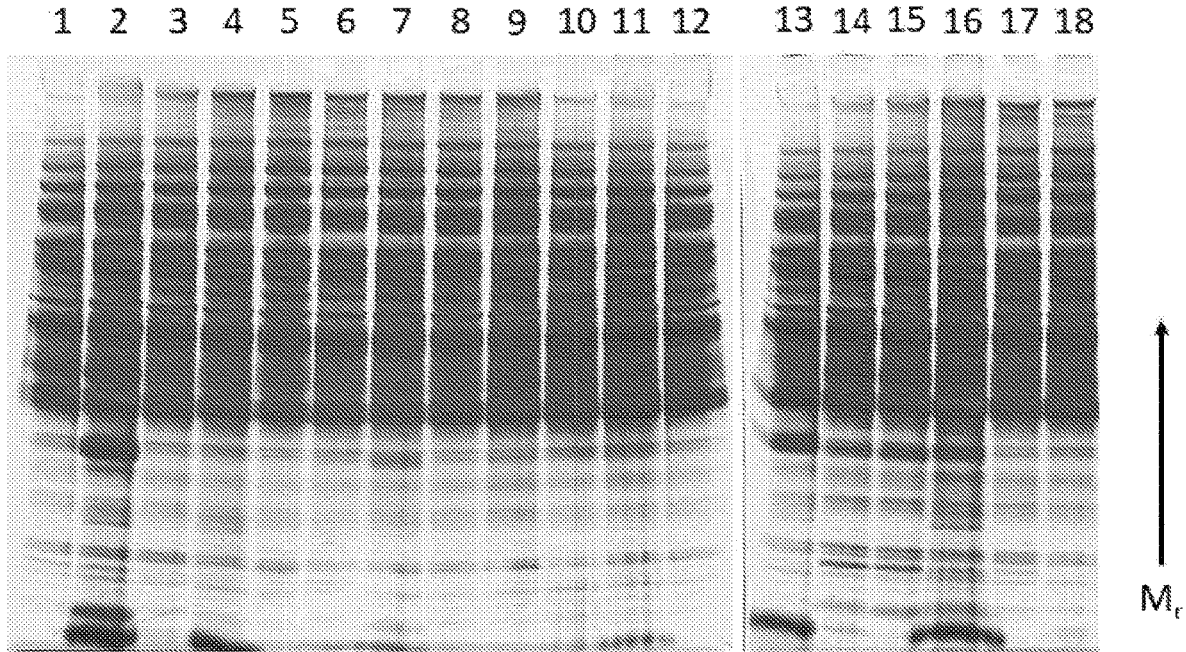
FIG. 1—Sodium dodecyl sulfate polyacrylamide gel electrophoresis (SDS-PAGE) analysis to confirm the quality of depletion of abundant serum proteins.

As set out above, the present invention is predicated, in part, on the identification of a protein (junction plakoglobin), the expression level of which is altered in blood of subjects with ovarian cancer, including early stage ovarian cancer. The differential expression of this protein indicates that it is a suitable biomarker which can form the basis of tests for detecting ovarian cancer in subjects, including detection of early stage ovarian disease.

Accordingly, certain disclosed embodiments of the present invention provide methods, compositions, products, and kits, that have one or more combinations of advantages. For example, some of the advantages of the embodiments disclosed herein include one or more of the following: a sensitive and specific biomarker for detecting ovarian cancer, including early stage ovarian cancer; an improved biomarker for ovarian cancer; an improved method for detecting ovarian cancer, including early stage ovarian cancer; an improved method for identifying a subject having ovarian cancer, including early stage ovarian cancer; a method for determining if a subject is susceptible to developing ovarian cancer; methods for treating ovarian cancer based on knowledge of the expression level of junction plakoglobin; methods for screening a candidate therapeutic agent for use in treating ovarian cancer; improved compositions and kits for detecting ovarian cancer; a method to identify biomarkers for cancer, including ovarian cancer; to address one or more problems in the art; to provide one or more advantages in the art; and/or to provide a useful commercial choice. Other advantages of certain embodiments are disclosed herein.

A biomarker is effectively an organic biomolecule which is differentially present in a sample taken from a subject of one phenotypic status (e.g. having a disease) as compared with another phenotypic status (e.g. not having the disease). A biomarker is differentially present between different phenotypic status groups if the mean or median expression level or amount of the biomarker is calculated to be different (e.g. higher or lower) between the groups. Therefore, biomarkers, alone or in combination, provide an indication that a subject belongs to one phenotypic status or another. With respect to biomarkers that are specific for a particular type of cancer, generally these would only be expected to be present in a subject having that cancer, but not present in a "normal" subject not having that cancer. However, it is to be made clear that the biomarker of the present invention (junction plakoglobin) is differentially expressed at the earliest stages of ovarian cancer development and therefore is present in higher amounts in affected subjects who considered themselves "normal" due to lack of phenotypic expression of the ovarian cancer.

Accordingly, in a first aspect, the present invention provides a method of detecting ovarian cancer in a subject, the method comprising:

(a) detecting an expression level of junction plakoglobin in blood of the subject;

(b) comparing the expression level of junction plakoglobin in the blood of the subject with a reference expression level for junction plakoglobin; and (c) detecting ovarian cancer in the subject on the basis of the comparison, wherein an expression level of junction plakoglobin in the blood of the subject that is higher than the reference expression level for junction plakoglobin indicates that the subject has ovarian cancer.

In a second aspect, the present invention provides a method of identifying a subject having ovarian cancer, the method comprising:

(a) detecting an expression level of junction plakoglobin in blood of the subject;

(b) comparing the expression level of junction plakoglobin in the blood of the subject with a reference expression level for junction plakoglobin; and (c) identifying the subject as a subject having ovarian cancer on the basis of the comparison, wherein an expression level of junction plakoglobin in the blood of the subject that is higher than the reference expression level for junction plakoglobin indicates that the subject has ovarian cancer.

As indicated above, the present inventors have determined that junction plakoglobin is differentially expressed in ovarian cancer, including at an early stage in the development of ovarian cancer. Accordingly, in a third aspect, the present invention provides a method of determining if a subject is susceptible to developing ovarian cancer, the method comprising:

(a) detecting an expression level of junction plakoglobin in blood of the subject;

(b) comparing the expression level of junction plakoglobin in the blood of the subject with a reference expression level for junction plakoglobin; and (c) determining if the subject is susceptible to developing ovarian cancer on the basis of the comparison, wherein an expression level of junction plakoglobin in the blood of the subject that is higher than the reference expression level for junction plakoglobin indicates that the subject is susceptible to developing ovarian cancer.

As used herein, the term "ovarian cancer" includes all stages of ovarian cancer, including early stage ovarian cancer. Early stage ovarian cancer may be Stage I or Stage II ovarian carcinoma. As would be understood by a person skilled in the art, the stage of a cancer is determined by the extent to which the cancer has spread. Stage I ovarian cancer is defined by the cancerous cells being localised to the ovary with the cancerous cells yet to spread to the pelvic surfaces or pelvic organs (Stage II), abdominal cavity or lymph nodes (Stage III), and distant organs (Stage IV). Accordingly, Stage I ovarian cancer is localised to one or both ovaries.

The meaning of "ovarian cancer" would be well understood by a person skilled in the art. For the avoidance of doubt, an ovarian cancer is a cancerous growth arising from the ovary. More than 90% of ovarian cancers are epithelial in origin given that they originate from the surface of the ovary. However, it is believed that the fallopian tubes and the peritoneum may also be the source of some ovarian cancers. Ovarian cancers are also categorised as gynaecological cancers.

In some embodiments of the various aspects of the present invention, the ovarian cancer is ovarian epithelial carcinoma. In some embodiments, the ovarian epithelial carcinoma is serous ovarian carcinoma, endometrioid ovarian carcinoma, mucinous ovarian carcinoma, or clear cell ovarian carcinoma.

As used herein, "junction plakoglobin" (also referred to herein as "JUP") refers to a member of the catenin family, given that it contains a distinct repeating amino acid motif called the armadillo repeat. Junction plakoglobin forms distinct complexes with cadherin and desmosomal cadherins and is a cytoplasmic component of desmosomes. Junction plakoglobin plays different cellular functions including structural roles and transcriptional activator roles. However, the role and regulation at the cellular level is complex and has not been fully elucidated.

Junction plakoglobin is also referred to in the art as JUP, CTNNG, DP3, DPIII, PDGB, PKGB, JUP-A, JUP-B, ARVD12, Catenin (cadherin-associated protein), gamma 80 kDa, desmoplakin III, Desmoplakin-3, and Catenin Gamma.

Details regarding junction plakoglobin may be accessed from a number of accessible database sources, including GeneCards (online at genecards.org/cgi-bin/carddisp.pl?gene=jup) and the GenBank database at the National Center for Biotechnology Information (NCBI) (online at_ncbi.nlm.nih.gov). For example, the Gene ID number for human junction plakoglobin is 3728. The human junction plakoglobin gene encodes seven isoform variants represented by GenBank Accession Numbers NM_002230.4 and NP_002221.1 (variant 1), NM_021991.3 and NP_068831.1 (variant 2), NM_001352773.1 and NP_001339702.1 (variant 3), NM_001352774.1 and NP_001339703.1 (variant 4), NM_001352775.1 and NP_001339704.1 (variant 5), NM_001352776.1 and NP_001339705.1 (variant 6), and NM_001352777.1 and NP_001339706.1 (variant 7). Variant 3 represents the longest transcript; however, variants 1 to 7 encode the same amino acid sequence. The nucleotide (mRNA) sequence (of variant 3) of human junction plakoglobin is represented by SEQ ID NO: 1, and the amino acid sequence of human junction plakoglobin is represented by SEQ ID NO: 2. The genomic DNA encompassing the human junction plakoglobin gene is represented by SEQ ID NO: 3 (GenBank Accession Number AH009840.2).

Further details of junction plakoglobin can be accessed from the UniProt database (online at uniprot.org) wherein the UniProt ID for human junction plakoglobin is P14923 (online at_uniprot.org/uniprot/P14923).

The junction plakoglobin gene has been found in numerous other species, including mouse, rat, cow, chicken, dog, pig, Rhesus monkey, cat, sheep, goat, rabbit, koala, horse, and frog. Further details of the junction plakoglobin gene in other species may be accessed from the GenBank database at NCBI. For example, the Gene ID number for mouse junction plakoglobin is 16480, for rat is 81679, for cow is 445543, for chicken is 429710, for dog is 480522, and for pig is 397592.

It is to be made clear that reference herein to junction plakoglobin includes a reference to its naturally-occurring variants. In this regard, a "variant" of junction plakoglobin may exhibit a nucleic acid or an amino acid sequence that is at least about 80% identical, at least about 85% identical, at least about 90% identical, at least about 91% identical, at least about 92% identical, at least about 93% identical, at least about 94% identical, at least about 95% identical, at least about 96% identical, at least about 97% identical, at least about 98% identical, at least about 99% identical, or at least about 99.9% identical to native junction plakoglobin. In some embodiments, a variant of junction plakoglobin is expected to retain native biological activity or a substantial equivalent thereof.

The methods of the aspects of the invention referred to throughout this description require detecting (measuring) an expression level of junction plakoglobin in blood of a subject. As would be understood by a person skilled in the art, junction plakoglobin is a functional biomolecule composed primarily of amino acids, with the amino acid sequence determined by a corresponding junction plakoglobin gene. Accordingly, as used herein, the term "detecting an expression level" of junction plakoglobin includes: (1) measuring the level of transcription of the corresponding junction plakoglobin gene into a messenger RNA (mRNA) molecule; and/or (2) measuring the level of translation of the mRNA into the protein (i.e. measuring the level of junction plakoglobin protein per se); and/or (3) measuring the level of activity of the translated protein. In effect, the expression level of junction plakoglobin can be measured at the RNA and/or protein stages of expression. In one embodiment the "expression level" of junction plakoglobin protein in blood of the subject may be a reflection of the extent of translation of the junction plakoglobin gene in the subject.

The term "biomarker" as used herein with respect to junction plakoglobin includes, but is not limited to, junction plakoglobin protein (polypeptide), junction plakoglobin polynucleotide (e.g. mRNA), and/or junction plakoglobin metabolites, whose expression level (e.g. level of transcription, level of translation, and/or level of activity) in blood of a subject with ovarian cancer, including early stage ovarian cancer, is higher than the expression level of junction plakoglobin in a normal sample, or in a benign ovarian tumour, (i.e. a reference expression level junction plakoglobin).

The term "gene" is to be understood to mean a region of genomic nucleotide sequence associated with a coding region which is transcribed and translated into the protein. Accordingly, the term "gene" with respect to junction plakoglobin may include regulatory regions (e.g. promoter regions), transcribed regions, protein coding exons, introns, untranslated regions and other functional and/or non-functional sequence regions associated with junction plakoglobin.

Measuring the level of junction plakoglobin protein (i.e. measuring the level of translation of junction plakoglobin mRNA into protein) in a subject can be achieved a number of ways as would be understood by a person skilled in the art. Exemplary methods include, but are not limited to, antibody-based (immunoassay-based) testing techniques (including Western blotting, immunoblotting, enzyme-linked immunosorbant assay (ELISA), "sandwich" immunoassays, radioimmunoassay (RIA), immunoprecipitation and dissociation-enhanced lanthanide fluoro immuno assay (DELFIA), precipitin reactions, gel diffusion precipitin reactions, immunodiffusion assays, immunoradiometric assays and protein A immunoassays), polystyrene and/or bead-based assays (such as Singleplex and Multiplex Luminex® assays), protein microarrays, mass spectrometry-based techniques (including liquid chromatography coupled to tandem mass spectrometry (LC-MS/MS), nano LC-MS/MS, matrix-assisted laser desorption/ionization mass spectrometry (MALDI-MS) as described in WO 2009/004576 (including surface enhanced laser desorption/ionization mass spectrometry (SELDI-MS), especially surface-enhanced affinity capture (SEAC), surface-enhanced need desorption (SEND) or surface-enhanced photo label attachment and release (SEPAR)), matrix-assisted laser desorption/ionization time-of-flight (MALDI-TOF) mass spectrometry, proteomics techniques, surface plasmon resonance (SPR), versatile fibre-based SPR, chemiluminescence, fluorescent polarization, phosphorescence, immunohistochemistry, immunofluorescence, microcytometry, microscopy, fluorescence activated cell sorting (FACS), and flow cytometry. Some of these techniques are described in further detail below.

With respect to antibody-based testing methods such as immunohistochemistry and immunoblotting, antibodies or antisera specific for junction plakoglobin can be used to detect protein levels. These techniques typically rely on the antibodies being detectably labelled. The antibody can be labelled by covalently or non-covalently combining the antibody with a substance or ligand that provides, or enables the generation of, a detectable signal. Some examples include, but are not limited to, radioactive isotopes, enzymes, fluorescent substances, luminescent substances, ligands, microparticles, redox molecules, substrates, cofactors, inhibitors, magnetic particles and the like. Examples of the radioactive isotopes include, but are not limited to, $^3$H, $^{12}$C, $^{13}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re. Examples of enzymes available as detection labels include, but are not limited to, β-glucuronidase, β-glucosidase, β-galactosidase, urease, peroxidase or alkaline phosphatase, acetylcholinesterase, glucose oxidase, hexokinase and GDPase, RNase, glucose oxidase and luciferase, phosphofructokinase, phosphoenolpyruvate carboxylase, aspartate aminotransferase, phosphoenolpyruvate decarboxylase, and β-lactamase. Examples of the fluorescent substances include, but are not limited to, fluorescin, isothiocyanate, rhodamine, phycoerythrin, phycocyanin, allophycocyanin, o-phthaldehyde and fluorescamin. Examples of luminescent substances include, but are not limited to, acridinium esters, luciferin and luciferase. Examples of ligands include, but are not limited to, biotin and its derivatives. Examples of the microparticles include, but are not limited to, colloidal gold and colored latex. Examples of the redox molecules include, but are not limited to, ferrocene, ruthenium complexes, viologen, quinone, Ti ions, Cs ions, diimide, 1,4-benzoquinone, hydroquinone, $K_4W(CN)_8$, $[Os(bpy)_3]^{2+}$, $[RU(bpy)_3]^{2+}$, and $[MO(CN)_8]^{4-}$. Alternatively, unlabelled primary antibody may be used in conjunction with a labelled secondary antibody that is specific for the primary antibody. Immunohistochemistry protocols and kits are well known in the art and are commercially available.

Also contemplated are traditional immunoassays including, for example, sandwich immunoassays including ELISA or fluorescence-based immunoassays, as well as other enzyme immunoassays. Nephelometry is an assay performed in liquid phase, in which antibodies to junction plakoglobin are in solution. Binding of junction plakoglobin protein to the antibody results in changes in absorbance, which are measured. In the SELDI-based immunoassay, a biospecific capture reagent for junction plakoglobin is attached to the surface of an MS probe, such as a pre-activated ProteinChip array (see below). The protein is then specifically captured on the biochip through this reagent, and the captured protein is detected by mass spectrometry (see below).

The term "antibody" is used herein in the broadest sense and encompasses intact polyclonal antibodies, intact monoclonal antibodies, antibody fragments (such as linear antibodies, single-chain antibody molecules, Fc or Fc' peptides, Fab, Fab', F(ab')2, and Fv fragments), single chain Fv (scFv) mutants, multispecific antibodies such as bispecific antibodies generated from at least two intact antibodies, fusion proteins comprising an antibody portion, and any other modified immunoglobulin molecule comprising an antigen recognition site so long as the antibodies exhibit the desired biological activity. An antibody can be one of any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations.

Naturally occurring immunoglobulins have a common core structure in which two identical light chains (about 24 kD) and two identical heavy chains (about 55 or 70 kD) form a tetramer. The amino-terminal portion of each chain is known as the variable (V) region and can be distinguished from the more conserved constant (C) regions of the remainder of each chain. Within the variable region of the light chain is a C-terminal portion known as the J region. Within the variable region of the heavy chain, there is a D region in addition to the J region. Most of the amino acid sequence variation in immunoglobulins is confined to three separate locations in the V regions known as hypervariable regions or complementarity determining regions (CDRs) which are directly involved in antigen binding. Proceeding from the amino-terminus, these regions are designated CDR1, CDR2 and CDR3, respectively. The CDRs are held in place by more conserved framework regions (FRs). Proceeding from the amino-terminus, these regions are designated FR1, FR2, FR3, and FR4, respectively. The locations of CDR and FR regions and a numbering system have been defined for example by Kabat et al., 1991 (Sequences of Proteins of Immunological Interest, Fifth Edition, U.S. Department of Health and Human Services, U.S. Government Printing Office).

The antigen binding part of the antibody is to be understood to mean the antigen-binding portion of the antibody molecule, including a Fab, Fab', F(ab')$_2$, Fv, a single-chain antibody (scFv), a chimeric antibody, a diabody or any polypeptide that contains at least a portion of an immunoglobulin that is sufficient to confer specific antigen binding, such as a molecule including one or more CDRs (see further detail below).

Antibodies exist as intact immunoglobulins or as a number of well-characterized fragments produced by digestion with various peptidases. Therefore, for example, pepsin digests an antibody below the disulfide linkages in the hinge region to produce F(ab)'$_2$, a dimer of Fab which itself is a light chain joined to V$_H$-C$_{H1}$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region. While various antibody fragments are defined in terms of the digestion of an intact antibody, a person skilled in the art would appreciate that such fragments may be synthesized de novo either chemically or by using recombinant DNA methodology. Therefore, the term antibody, as used herein, also includes antibody fragments either produced by the modification of whole antibodies, or those synthesized de novo using recombinant DNA methodologies (e.g. single chain Fv) or those identified using phage display libraries (see for example McCafferty et al., 1990, *Nature* 348: 552-554).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g. an enzyme, toxin, hormone, growth factor, drug, etc.; or (b) the variable region, or a portion thereof, is altered, replaced or exchanged with a variable region having a different or altered antigen specificity. The chimeric antibodies may be monovalent, divalent, or polyvalent immunoglobulins. For example, a monovalent chimeric antibody is a dimer (HL) formed by a chimeric H chain associated through disulfide bridges with a chimeric L chain, as noted above. A divalent chimeric antibody is a tetramer (H$_2$ L$_2$) formed by two HL dimers associated through at least one disulfide bridge. A polyvalent chimeric antibody is based on an aggregation of chains.

In some embodiments, the antibody may be a humanised antibody. A "humanised" antibody is an antibody that retains the reactivity of a non-human antibody while being less immunogenic in humans. This can be achieved, for example, by retaining the non-human CDR regions and replacing the remaining parts of the antibody with their human counterparts. See for example Morrison et al., 1984, *Proc. Natl. Acad. Sci. USA*, 81: 6851-6855; Morrison and Oi, 1988, *Adv. Immunol.*, 44: 65-92; Verhoeyen et al., 1988, *Science*, 239: 1534-1536; Padlan, 1991, *Molec. Immun.*, 28: 489-498; and Padlan, 1994, *Molec. Immun.*, 31: 169-217.

In some embodiments, the antibody may be a fully human antibody. As would be understood by a person skilled in the art, a fully human antibody is an antibody in which both the variable and constant regions are of human origin. Methods for producing or identifying such antibodies are described below.

Additional antibody types are also contemplated by the present invention. These include antibodies sourced from a non-mammalian animal such as a cartilaginous fish (e.g. shark IgNAR antibodies—see WO2012/073048) or modified human protein scaffolds that provide functionality similar to shark antibodies, such as i-bodies which have binding moieties based on shark IgNAR antibodies (see WO2005/118629). IgNARs are disulphide-bonded homodimers consisting of five constant domains (CNAR), one variable domain (VNAR), and no light chains (Greenberg et al., 1995, *Nature* 374: 168-173; Nuttall et al., 2001, *Mol. Immunol.*, 38: 313-326; Diaz et al., 2002, *Immunogenetics* 54: 501-512; and Nuttall et al., 2003, *Eur. J. Biochem.*, 270: 3543-3554). Antibodies sourced from camels (camelid antibodies), dromedaries and llamas are also contemplated by the present invention. Such antibodies consist of only two heavy chains and are devoid of light chains. Due to the heavy chain dimer structure of camelid and shark antibodies, they are sometimes termed "heavy-chain mini-antibodies" (mnHCAbs) or "mini-antibodies" (mnAbs) (Holliger and Hudson, 2005, *Nat. Biotechnol.*, 23(1): 1126-1136). Without the light chain, these antibodies bind to their antigens by a single domain—the variable antigen binding domain of the heavy chain immunoglobulin, referred to as Vab (camelid antibodies) or VNAR (shark antibodies).

Affibodies are also contemplated by the present invention. Affibody molecules are a class of affinity proteins based on a 58-amino acid residue protein domain, derived from one of the IgG-binding domains of staphylococcal protein A. This three helix bundle domain has been used as a scaffold for the construction of combinatorial phagemid libraries, from which Affibody variants that target the desired molecules can be selected using phage display technology (Nord K et al., 1997, *Nat. Biotechnol.*, 15: 772-777; Ronmark J et al., 2002, *Eur. J. Biochem.*, 269: 2647-2655). Further details about Affibodies and methods of production thereof are also disclosed in U.S. Pat. No. 5,831,012.

Antibodies for any of the methods and applications referred to herein can be produced according to well-established techniques in the art. For example, various hosts including rabbits, rats, goats, mice, humans, and others may be immunised by injection with junction plakoglobin polypeptide or with any fragment, peptide or oligopeptide thereof which has immunogenic properties. Various adjuvants may be used to increase immunological response and include, but are not limited to, Freund's, mineral gels such as aluminum hydroxide, and surface-active substances such as lysolecithin. Adjuvants used in humans include BCG (bacilli Calmette-Guerin) and *Corynebacterium parvum*.

It is preferred that junction plakoglobin oligopeptides, peptides, or fragments used to induce antibodies, have an amino acid sequence consisting of at least 5 amino acids, and, more preferably, of at least 10 amino acids of junction plakoglobin. It is also preferable that these oligopeptides, peptides, or fragments are identical to a portion of the amino acid sequence of the natural protein and contain the entire amino acid sequence of a small, naturally occurring molecule. Short stretches of amino acids from junction plakoglobin may be fused with those of another protein, such as keyhole limpet haemocyanin (KLH), and antibodies to the chimeric molecule may be produced.

Monoclonal antibodies to junction plakoglobin may be prepared using any technique which provides for the production of antibody molecules by continuous cell lines in culture. These include, but are not limited to, the hybridoma technique, the human B-cell hybridoma technique, and the EBV-hybridoma technique (for example, see Kohler et al., 1975, *Nature* 256: 495-497; Kozbor et al., 1985, *J. Immunol. Methods* 81:31-42; Cote et al., 1983, *Proc. Natl. Acad. Sc. USA* 80: 2026-2030; and Cole et al., 1984, *Mol. Cell Biochem.* 62: 109-120).

Antibodies may also be produced by inducing in vivo production in the lymphocyte population or by screening immunoglobulin libraries or panels of highly specific binding reagents as disclosed in the literature (for example, see Orlandi et al., 1989, *Proc. Natl. Acad. Sci. USA* 86: 3833-3837; and Winter and Milstein, 1991, *Nature* 349: 293-299). Antibodies may also be generated using phage display. For example, functional antibody domains are displayed on the surface of phage particles that carry the polynucleotide sequences encoding them. Such phage can be utilized to display antigen-binding domains expressed from a repertoire or combinatorial antibody library (e.g. human or murine). Phage expressing an antigen binding domain that binds junction plakoglobin can be selected or identified using the junction plakoglobin protein or a portion thereof. Phage used in these methods are typically filamentous phage including fd and MI 3 binding domains expressed from phage with Fab, Fv or disulfide stabilised Fv antibody domains recombinantly fused to either the phage gene III or gene VIII protein. Examples of phage display methods that can be used to make junction plakoglobin antibodies may include those disclosed in Brinkman et al., 1995, *J. Immunol. Methods* 182: 41-50; Ames et al., 1995, *J. Immunol. Methods* 184: 177-186; Kettleborough et al., 1994, *Eur. J. Immunol.* 24: 952-958; Persic et al., 1997, *Gene* 187: 9-18; Burton et al., 1994, *Advances in Immunology* 57: 191-280; PCT application number PCT/GB91/01134; PCT publications numbers WO 90/02809; WO 91/10737; WO 92/01047; WO 92/18619; WO 93/11236; WO 95/15982; WO 95/20401; and U.S. Pat. Nos. 5,698,426; 5,223,409; 5,403, 484; 5,580,717; 5,427,908; 5,750,753; 5,821,047; 5,571, 698; 5,427,908; 5,516,637; 5,780,225; 5,658,727; 5,733,743 and 5,969,108; each of which is incorporated herein by reference in its entirety.

Techniques which can be used to produce single-chain Fvs and antibodies include those described in U.S. Pat. Nos. 4,946,778 and 5,258,498; Huston et al., 1991, *Methods in Enzymology* 203: 46-88; Shu et al., 1993, *Proc. Natl. Acad. Sci. USA* 90: 7995-7999; and Skerra et al., 1988, *Science* 240: 1038-1040.

Antibody fragments which contain specific binding sites for junction plakoglobin may be generated using standard techniques known in the art. For example, F(ab')2 fragments may be produced by pepsin digestion of a junction plakoglobin antibody molecule and Fab fragments generated by reducing the disulfide bridges of the F(ab')2 fragments. Alternatively, Fab expression libraries may be constructed to allow rapid and easy identification of monoclonal Fab fragments with the desired specificity (for example, see Huse et al., 1989, *Science* 246: 1275-1281).

Fully human junction plakoglobin antibodies may be produced using a number of techniques. These include using display technologies as mentioned above in which human antibodies or antibody fragments are displayed on the surface of a phage for example. In another method (Lonberg N, 2008, *Handb. Exp. Pharmacol.*, 69-97), first generation human antibodies to junction plakoglobin may be produced by utilising transgenic animals that produce antibodies from human genes. When challenged with an antigen (i.e. junction plakoglobin or an oligopeptide, peptide, or fragment thereof), these animals produce human antibodies avoiding the humanisation steps. Human antibodies can also be produced from B cells isolated from humans using a technique described in Crowe J E Jr, 2009, *Vaccine* 27: 47-51. Other techniques for human antibody production are described in PCT international publication number WO 2013/168150 and Duvall M et al., 2011, *mAbs* 3(2): 203-208, amongst others. For example, Duvall et al utilises technology which produces human IgG antibody libraries from naïve B cells isolated from human tonsil tissue. The antibodies are produced from human genes and are therefore 100% human antibodies.

Antibodies to junction plakoglobin protein may also be purchased from commercial sources. In this regard, pre-prepared ELISA kits containing antibody specific for human junction plakoglobin detection are available from MyBio-source (San Diego, California, USA-online at mybiosource-.com/jup-human-elisa-kits/junction-plakoglobin/765744), antibodies-online Inc. (Limerick, Pennsylvania, USA—on-line at antibodies-online.com/cell-cell-junction-organiza-tion-pathway-74/jup-elisa-kit-3920/), and LifeSpan BioScience, Inc. (Seattle, Washington, USA—online at lsbio.com/ elisakits/human-jup-ctnng-junction-plakoglobin-elisa-kit-sandwich-elisa-ls-f7467/7467). Additional commercial sources of antibodies to junction plakoglobin protein may also be obtained from GeneCards (online at genecards.org/ cgi-bin/carddisp.pl?gene=JUP).

A further technique for measuring the level of junction plakoglobin protein using an antibody-based platform involves the versatile fibre-based surface plasmon resonance (VeSPR) biosensor, as described in PCT International Publication No. WO 2011/113085. Traditional SPR is a well-established method for label-free bio-sensing that relies on the excitation of free electrons at the interface between a dielectric substrate and a thin metal coating. The condition under which the incoming light couples into the plasmonic wave depends on the incidence angle and the wavelength of the incoming light as well as the physical properties (dielectric constant/refractive index) of the sensor itself and the surrounding environment. For this reason, SPR is sensitive to even small variations in the density (refractive index) in the close vicinity of the sensor, and does not require the use of fluorescent labels. The small variation of refractive index induced by the binding biomolecules such as proteins onto the sensor surface, can be measured by monitoring the coupling conditions via either the incidence angle or the wavelength of the incoming light. Existing SPR systems use the bulky and expensive Krestchmann prism configuration where one side of the prism is coated with a metal such as gold or silver that can support a plasmonic wave. Alternative SPR architectures have been developed based on optical fibres with the metallic coating deposited around a short section of the fibre. This approach reduces the complexity and cost of such sensors, opening a pathway to distinctive applications such as dip sensing. The material at the sensor surface is probed by monitoring the wavelength within a broad spectrum that is absorbed due to coupling to the surface plasmon. These techniques suffer from practical limitations associated with the need for careful temperature calibration, causing difficulty in analysing large numbers of samples consistently. VeSPR is a powerful variant of an optical-fibre based SPR sensor. VeSPR has a number of demonstrated advantages over existing SPR techniques including: (i) higher signal-to-noise ratio thus higher sensitivity; (ii) self-referencing of the transducing signal thus avoiding expensive/bulky temperature control; and (iii) the ability to perform multiplexed detection of different analytes using a single fibre.

Proteomics can also be used to measure the level of junction plakoglobin protein in a sample at a certain point of time. In particular, proteomic techniques can be used to assess the global changes of protein expression in a sample (also referred to as expression proteomics). Proteomic analysis typically includes: (i) separation of individual proteins in a sample by 2-D gel electrophoresis (2-D PAGE); (ii) identification of the individual polypeptides recovered from the gel, for example by mass spectrometry or N-terminal sequencing; and (iii) analysis of the data using bioinformatics.

Protein microarrays (also termed biochips) may also be used to determine the level of junction plakoglobin protein in a sample. Many protein biochips are described in the art, including for example protein biochips produced by Ciphergen Biosystems, Inc. (Fremont, CA), Zyomyx (Hayward, CA), Invitrogen (Carlsbad, CA), Biacore (Uppsala, Sweden) and Procognia (Berkshire, UK). Examples of such protein biochips are described in the following patents or published patent applications: U.S. Pat. Nos. 6,225,047, 6,537,749, 6,329,209, and 5,242,828, and PCT International Publication Nos. WO 00/56934 and WO 03/048768.

The level of junction plakoglobin protein can also be measured by mass spectrometry, a method that employs a mass spectrometer to detect gas phase ions. Examples of mass spectrometers are time-of-flight, magnetic sector, quadrupole filter, ion trap, ion cyclotron resonance, electrostatic sector analyzer and hybrids of these. The mass spectrometer may be a laser desorption/ionization mass spectrometer. In laser desorption/ionization mass spectrometry, a sample containing the junction plakoglobin protein is placed on the surface of a mass spectrometry probe, a device adapted to engage a probe interface of the mass spectrometer and to present the protein to ionizing energy for ionization and introduction into a mass spectrometer. A laser desorption mass spectrometer employs laser energy, typically from an ultraviolet laser, but also from an infrared laser, to desorb analytes from a surface, to volatilize and ionize them and make them available to the ion optics of the mass spectrometer. The analysis of junction plakoglobin protein by LDI can take the form of matrix-assisted laser desorption/ionization (MALDI—as described for example in Karas M and Hillenkamp F, 1988, *Anal. Chem.*, 60: 2299-2301; Tanaka K et al., 1988, *Rapid Commun. Mass Spectrom.*, 2: 151-153; and Norris J L and Caprioli R M, 2013, *Chem Rev.*, 113: 2309-2342) or of surface-enhanced laser desorption/ionization (SELDI—as described for example in Hutchens T and Yip T, 1993, *Rapid Commun. Mass Spectrom.*, 7: 576-580; Tang N et al., 2004, *Mass Spec. Reviews*, 23: 34-44; and U.S. Pat. Nos. 5,719,060 and 6,225,047).

Other laser desorption mass spectrometry methods which may be employed include surface-enhanced neat desorption (SEND—as described for example in U.S. Pat. No. 6,124, 137 and PCT International Publication No. WO 03/64594), SEAC/SEND (a version of laser desorption mass spectrometry in which both a capture reagent and an energy absorbing molecule are attached to the sample presenting surface), and surface-enhanced photolabile attachment and release (SEPAR—which involves the use of probes having moieties attached to the surface that can covalently bind junction plakoglobin protein, and then release the protein through breaking a photolabile bond in the moiety after exposure to light, e.g. to laser light).

As indicated above, liquid chromatography coupled to tandem mass spectrometry (LC-MS/MS) is another method by which the level of junction plakoglobin protein in a sample can be determined. LC-MS/MS offers a number of advantages for clinical diagnosis over traditional technologies. These advantages include the speed of assay development, the relatively low cost-per-assay whether there is one or many analytes in a single sample, high specificity, and no costly analyte-specific reagents (ASRs) are required.

With respect to measuring the level of activity of junction plakoglobin protein, assays which exploit the activity of junction plakoglobin may be employed. For example, junction plakoglobin forms distinct complexes with cadherin and desmosomal cadherins. Therefore, assays which measure for formation of desmosomal cadherin clusters on the surface of cells, or formation of desmosomal-like junctions, will be a reflection of the level and/or activity of junction plakoglobin in a particular sample. Plakoglobin also plays an important role in several signaling cascades during the processes of cell motility, cell proliferation, and apoptosis. All these processes involve the interaction of cytoplasmic plakoglobin with various kinases and the inhibition of Wnt-$\beta$-catenin signaling by nuclear plakoglobin. Accordingly, methods which assay for plakoglobin/kinase interaction, or inhibition of Wnt-$\beta$-catenin signaling, may be used to detect the level and/or activity of junction plakoglobin protein. These are non-limiting examples and any other method which exploits the activity of junction plakoglobin may be employed.

Methods for measuring the level of transcription of the junction plakoglobin gene into mRNA are also known in the art. For example, levels of mRNA may be measured by techniques which include, but are not limited to, Northern blotting, RNA in situ hybridisation, reverse-transcriptase PCR (RT-PCR), real-time (quantitative) RT-PCR, microarrays, or "tag based" technologies such as SAGE (serial analysis of gene expression). Microarrays and SAGE may be used to simultaneously quantitate the expression of more than one gene. Primers or probes may be designed based on nucleotide sequences of the genes or transcripts thereof. Methodology similar to that disclosed in Paik et al., 2004 (*NEJM*, 351(27): 2817-2826), or Anderson et al., 2010 (*Journal of Molecular Diagnostics*, 12(5): 566-575) may be used to measure the expression of junction plakoglobin. Many methods are also disclosed in standard molecular biology text books such as Green M R and Sambrook J, *Molecular Cloning: A Laboratory Manual* (4th edition), Cold Spring Harbor Laboratory Press, 2012.

With respect to RT-PCR, the first step is typically the isolation of total RNA from a sample obtained from the subject under investigation. A typical sample in this instance would be an ovarian vein blood sample, although other sample sources are contemplated as described below. If the source of RNA is from a tumour, RNA can also be extracted, for example, from frozen or archived paraffin-embedded and fixed (e.g. formalin-fixed) tissue samples previously obtained from the subject. Messenger RNA (mRNA) may be subsequently purified from the total RNA sample. The total RNA sample (or purified mRNA) is then reverse transcribed into cDNA using a suitable reverse transcriptase. The reverse transcription step is typically primed using oligo-dT primers, random hexamers, or primers specific for the junction plakoglobin gene, depending on the RNA template. The cDNA derived from the reverse transcription reaction then serves as a template for a typical PCR reaction. In this regard, two oligonucleotide PCR primers specific for the junction plakoglobin gene are used to generate a PCR product. A third oligonucleotide, or probe, designed to detect a nucleotide sequence located between the other two PCR primers is also used in the PCR reaction. The probe is non-extendible by the Taq DNA polymerase enzyme used in the PCR reaction, and is labelled with a reporter fluorescent dye and a quencher fluorescent dye. Any laser-induced emission from the reporter dye is quenched by the quenching dye when the two dyes are located close together, as they are on the probe. During the PCR amplification reaction, the Taq DNA polymerase enzyme cleaves the probe in a template-dependent manner. The resultant probe fragments disassociate in solution, and signal from the released reporter dye is freed from the quenching effect of the second fluorophore. One molecule of reporter dye is liberated for each new molecule synthesized, and detection of the unquenched reporter dye provides the basis for quantitative interpretation of the data.

In real-time RT-PCR the amount of product formed, and the timing at which the product is formed, in the PCR reaction correlates with the amount of starting template. RT-PCR product will accumulate quicker in a sample having an increased level of mRNA compared to a standard or "normal" sample. Real-time RT-PCR measures either the fluorescence of DNA intercalating dyes such as Sybr Green into the synthesized PCR product, or can measure PCR product accumulation through a dual-labelled fluorogenic probe (i.e. TaqMan probe). The progression of the RT-PCR reaction can be monitored using PCR machines such as the Applied Biosystems' Prism 7000 or the Roche LightCycler which measure product accumulation in real-time. Real-time RT-PCR is compatible both with quantitative competitive PCR and with quantitative comparative PCR. The former uses an internal competitor for each target sequence for normalization, while the latter uses a normalization gene contained within the sample, or a housekeeping gene for RT-PCR.

The production and application of microarrays for measuring the level of expression of a gene at the transcriptional level are well known in the art. In general, in a microarray, a nucleotide sequence (for example an oligonucleotide, a cDNA, or genomic DNA) representing a portion, or all, of the junction plakoglobin gene would occupy a known location on a substrate. Typically, the substrate includes a multitude of nucleotide sequences such that junction plakoglobin and one or more other relevant genes can be assayed simultaneously. A nucleic acid target sample (for example total RNA or mRNA) obtained from a subject of interest is then hybridized to the microarray and the amount of target nucleic acid hybridized to each probe on the array is quantified and compared to the hybridisation which occurs to a standard or "normal" sample. One exemplary quantifying method is to use confocal microscope and fluorescent labels. The Affymetrix GeneChip™ Array system (Affymetrix, Santa Clara, California, USA) and the Atlas™ Human cDNA Expression Array system are particularly suitable for quantifying the hybridization; however, it will be apparent to those of skill in the art that any similar systems or other effectively equivalent detection methods can also be used. Fluorescently labelled cDNA probes may also represent the nucleic acid target sample. Such probes can be generated through incorporation of fluorescent nucleotides during reverse transcription of total RNA or mRNA extracted from a sample of the subject to be tested. Labelled cDNA probes applied to the microarray will hybridize with specificity to the equivalent spot of DNA on the array. Quantitation of hybridization of each arrayed element allows for assessment of corresponding mRNA abundance in the sample compared to the abundance observed in a standard or "normal" sample.

With dual colour fluorescence, separately labelled cDNA probes generated from two sources of RNA are hybridized pairwise to the array. The relative abundance of the transcripts from the two sources corresponding to each specified gene is thus determined simultaneously. The miniaturized scale of the hybridization using microarray analysis affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels.

In the subject, the expression level of junction plakoglobin may be measured directly in the subject, or in an alternative embodiment, the expression level of junction plakoglobin may be measured in a sample obtained from a subject. It is to be made clear that the sample obtained from the subject that is analysed by the methods of the present invention may have previously been obtained from the subject, and, for example, may have been stored in an appropriate repository. In this instance, the sample would have been obtained from the subject in isolation of, and therefore separate to, the methods of the present invention. Accordingly, the methods of the aforementioned aspects of the invention can be practiced wholly in vitro.

The sample which is obtained from the subject may include, but is not limited to, a blood sample (such as a peripheral blood sample or central venous catheter sample), or a sample derived from blood (for example a plasma sample or serum sample or a fraction of a blood, serum sample or plasma sample), cervical pap smears, ascites, bladder washing, uterine washing, and a tissue sample from one or both ovaries, one or both fallopian tubes, or metastatic tumour tissue of the subject. In certain circumstances, the sample may be manipulated in any way after procurement, such as by treatment with reagents, solubilization, or enrichment for certain components, such as the relevant protein or polynucleotide under investigation.

In some embodiments of the various aspects of the present invention, the sample is a serum sample or plasma sample obtained from blood of the subject. Blood plasma is the pale-yellow liquid component of blood, in which the blood cells in whole blood would normally be suspended. It makes up about 55% of the total blood volume. It is mostly water (up to 95% by volume) and contains dissolved proteins, glucose, clotting factors, mineral ions, hormones and carbon dioxide. Blood plasma is prepared by spinning a tube of fresh blood in a centrifuge until the blood cells fall to the bottom of the tube. The blood plasma is then poured or drawn off. Blood plasma, preferably supplemented with a clotting inhibitor, e.g. heparin or EDTA, has a density of approximately 1.025 kg/1. Blood serum is blood plasma without fibrinogen or the other clotting factors (i.e., whole blood minus both the cells and the clotting factors).

In the methods of the aforementioned aspects of the invention, once the expression level of junction plakoglobin has been detected (measured) in blood of the subject, or in a blood sample obtained from the subject, the expression level is compared to a reference expression level for junction plakoglobin (for example an expression level for junction plakoglobin associated with a normal or non-affected control subject).

In specific embodiments, the inventors have found that the expression level of junction plakoglobin is higher in blood of subjects with ovarian cancer, including those diagnosed as having early stage ovarian cancer, compared with blood of normal healthy controls (i.e. subjects that have no evidence of ovarian cancer) and/or compared with blood from a benign ovarian tumour. Accordingly, an expression level of junction plakoglobin in a subject which is higher than a reference expression level for junction plakoglobin is indicative of ovarian cancer (including early stage ovarian cancer) in the subject, or indicates that the subject is susceptible to developing ovarian cancer.

Reference herein to "higher" with respect to the expression level of junction plakoglobin, whether at the translational (protein) or transcriptional (mRNA) stage, is intended to mean, for example, at least about a 1%, 5%, 10%, 20%, 30%, 40%, 50%, 60%, 70%, 80%, 90%, 100%, 1.1-fold, 1.2-fold, 1.3-fold, 1.4-fold, 1.5-fold, 1.6-fold, 1.7-fold, 1.8-fold, 1.9-fold, 2-fold, 2.1-fold, 2.2-fold, 2.3-fold, 2.4-fold, 2.5-fold, 2.6-fold, 2.7-fold, 2.8-fold, 2.9-fold, 3-fold, 3.1-fold, 3.2-fold, 3.3-fold, 3.4-fold, 3.5-fold, 3.6-fold, 3.7-fold, 3.8-fold, 3.9-fold, 4-fold, 5-fold, 10-fold, 20-fold, 50-fold, 100-fold or greater, increase in the expression level of junction plakoglobin compared to the reference expression level.

As indicated above, in the context of the present invention the reference expression level for junction plakoglobin is a level of junction plakoglobin which is known to be found in blood from a subject not suffering from ovarian cancer (i.e. a "normal" subject). In this instance, a reference expression level for junction plakoglobin may be derived from blood of a normal subject, or may be derived from an average of the level of junction plakoglobin in blood from a number of normal subjects (e.g. n=2 to 100 or more), wherein the subject or subjects have no prior history of ovarian cancer. A reference expression level for junction plakoglobin can also be obtained from one or more "normal" samples from a subject suspected to have, or which has, ovarian cancer. For example, a reference expression level for junction plakoglobin may be obtained from at least one peripheral vein blood sample, and is preferably obtained from an average of peripheral vein blood samples (e.g. n=2 to 100 or more), wherein the subject or subjects are suspected of having, or which have, ovarian cancer. Furthermore, a reference expression level for junction plakoglobin may be a level of junction plakoglobin that is present in blood from a subject having a benign ovarian tumour. In this instance, the reference expression level for junction plakoglobin would be derived from blood of a subject having at least one benign ovarian tumour, or may be derived from an average of the level of junction plakoglobin in a number of benign ovarian tumours from the same or different subjects (e.g. n=2 to 100 or more).

In the methods of the aforementioned aspects of the invention, the expression level of one or more additional biomarkers known to be associated with ovarian cancer may also be assessed. Detecting the expression level of particular combinations of biomarkers may provide greater sensitivity, specificity and predictive power than any one biomarker alone. Accordingly, in some embodiments of the present invention, the expression level of junction plakoglobin may be detected in blood of a subject to be tested in combination with the blood expression level of tumour associated antigen CA125 and/or human epididymis protein 4 (HE4) in the subject.

CA125 is encoded by the MUC16 gene and is a large transmembrane glycoprotein that was first identified using the monoclonal antibody 00125 in human ovarian carcinoma cell lines. The CA125 protein is characterised by a large extracellular domain containing up to 60 tandem repeats of 156 amino acids, and harbours the epitope for the original 00125 monoclonal antibody, as well as a heavily glycosylated amino terminal region. The molecular function of the CA125 protein has yet to be determined but it has been shown to function as a calcium dependent protease, and its presence in embryonic membranes as well as its heavily glycosylated extracellular domain may allow it to have a role in the motility and metastatic potential of ovarian carcinoma.

The MUC16 gene has been found in a number of species, including human, rat, mouse, chimpanzee, cheetah, and monkey. MUC16 is also referred to in the art as CA125, mucin-16, CA125 ovarian cancer antigen, ovarian cancer-related tumour marker CA125 and ovarian carcinoma antigen CA125. Details regarding MUC16 may be accessed from the GenBank database at the National Center for Biotechnology Information (NCBI) (online at ncbi.nlm.nih-.gov). For example, the Gene ID number for human MUC16 is 94025. The human MUC16 gene is represented by GenBank Accession Number NM_024690.2 and the encoded protein by NP_078966.2 Further details of the MUC16 gene in other species may be accessed from the NCBI. For example, the Gene ID number for rat MUC16 is 315451, for mouse is 73732, for chimpanzee is 744458, for cheetah is 106979012, and for monkey is 105705887. Further details regarding the MUC16 gene in humans and other species can also be accessed from the UniProt database (online at uniprot.org) wherein the UniProt ID for human MUC16 is Q8WX17 (online at_uniprot.org/uniprot/Q8WX17).

Human epididymis protein 4 (HE4) is encoded by the WFDC2 gene which is a member of the WFDC domain family of proteins. The WFDC domain, or WAP Signature motif, contains eight cysteines forming four disulfide bonds at the core of the protein, and functions as a protease inhibitor in many family members. WFDC2 is also known as HE4, WAP5, EDDM4, dJ461P17.6, WAP four-disulfide core domain protein 2, WAP domain containing protein HE4-V4, epididymal protein 4, epididymal secretory protein E4, epididymis secretory sperm binding protein, epididymis-specific, whey-acidic protein type, four-disulfide core, major epididymis-specific protein E4, and putative protease inhibitor WAP5.

Details regarding WFDC2 may be accessed from the GenBank database at the National Center for Biotechnology Information (NCBI) (online at_ncbi.nlm.nih.gov). For example, the Gene ID number for human WFDC2 is 10406. The human WFDC2 gene is represented by GenBank Accession Number NM_006103.4 and the encoded protein by NP_006094.3. Further details of the WFDC2 gene in other species may be accessed from the NCBI. For example, the Gene ID number for rat WFDC2 is 286888, for mouse is 67701, for chimpanzee is 458283, for cow is 618044, and for monkey is 710469. Further details regarding the WFDC2 gene in humans and other species can also be accessed from the UniProt database (online at uniprot.org) wherein the UniProt ID for human WFDC2 is Q14508 (online at uniprot.org/uniprot/Q14508).

As used herein, the term "subject" refers to any animal (e.g. a mammal), including, but not limited to humans, non-human primates, dogs, horses, cattle, sheep, pigs, rodents, and any other animal known to get ovarian cancer. Therefore, it should be appreciated that the methods of the present invention are not limited to humans. Details of junction plakoglobin in other species, and their associated amino acid and mRNA sequences, may be readily accessed from the GenBank and UniProt databases (as discussed above) or sequences may be identified by BLAST searching using the human junction plakoglobin sequence.

In some embodiments of the aforementioned aspects of the invention, the methods further comprise treating a subject in which ovarian cancer has been detected, or treating a subject which has been identified as having ovarian cancer. Accordingly, in a fourth aspect the present invention provides a method of treating ovarian cancer in a subject, comprising:

(a) identifying the subject as a subject with ovarian cancer on the basis that an expression level of junction plakoglobin in blood of the subject is higher than a reference expression level for junction plakoglobin; and (b) treating ovarian cancer in the subject.

In some embodiments, the subject referred to in step (a) may have been previously determined to have an expression level of junction plakoglobin indicative of ovarian cancer. The expression level of junction plakoglobin may have been determined using the methods referred to above.

In a fifth aspect, the present invention provides a method of treating ovarian cancer in a subject, comprising:

(a) detecting an expression level of junction plakoglobin in blood of the subject;

(b) comparing the expression level of junction plakoglobin in the blood of the subject with a reference expression level for junction plakoglobin;

(c) detecting ovarian cancer in the subject on the basis of the comparison, wherein an expression level of junction plakoglobin in the blood of the subject that is higher than the reference expression level for junction plakoglobin is indicative of ovarian cancer in the subject; and (d) treating ovarian cancer in the subject.

With respect to the fifth aspect of the invention, steps (a), (b) and (c) may be performed as indicated above with respect to the first aspect of the present invention.

In some embodiments of the aforementioned aspects of the present invention, treating ovarian cancer in the subject refers to the use of agents and techniques, alone or in combination, based on the type and stage of the ovarian cancer. In some embodiments, surgery may be required. For example, a laparotomy may be employed to locate and remove as much of the tumour as possible from the affected ovary or ovaries. In some embodiments, one or both ovaries of the subject may be removed. In advanced stages of ovarian cancer, the Fallopian tube(s), uterus, omentum, appendix, associated lymph glands, and/or some of the bowel, may also need to be removed from an affected subject.

In some embodiments, treatment may comprise one or more of chemotherapy, radiotherapy, gene therapy, hormone therapy, immunotherapy, and antisense oligonucleotide therapy. One or more of these therapies may be combined with a surgical procedure as described above. A person skilled in the art would be able to select an appropriate treatment step, or combination of therapies based on the type of tumour being treated, the subjects clinical history, overall condition, and other factors. A combination of therapies refers to either concurrent or sequential administration of each therapy to the subject.

Chemotherapeutic agents may include, but are not limited to, alkylating agents, such as nitrogen mustards (for example, chlorambucil, chlormethine, cyclophosphamide, ifosfamide, and melphalan), nitrosoureas (for example, carmustine, fotemustine, lomustine, and streptozocin), platinum compounds (for example, carboplatin, cisplatin, oxaliplatin, and BBR3464), busulfan, dacarbazine, mechlorethamine, procarbazine, temozolomide, thiotepa, and uramustine; antimetabolites, such as folic acid (for example, methotrexate, pemetrexed, and raltitrexed), purine (for example, cladribine, clofarabine, fludarabine, mercaptopurine, and thioguanine), pyrimidine (for example, capecitabine), cytarabine, fluorouracil, and gemcitabine; plant alkaloids, such as podophyllum (for example, etoposide, and teniposide), taxane (for example, docetaxel and paclitaxel), vinca (for example, vinblastine, vincristine, vindesine, and vinorelbine); cytotoxic/anti-tumor antibiotics, such as anthracycline family members (for example, daunorubicin, doxorubicin, epirubicin, idarubicin, mitoxantrone, and valrubicin), bleomycin, hydroxyurea, and mitomycin; topoisomerase inhibitors, such as topotecan and irinotecan; monoclonal antibodies, such as alemtuzumab, bevacizumab, cetuximab, gemtuzumab, rituximab, panitumumab, and trastuzumab; photosensitizers, such as aminolevulinic acid, methyl aminolevulinate, porfimer sodium, and verteporfin; and other agents, such as alitretinoin, altretamine, amsacrine, anagrelide, arsenic trioxide, asparaginase, bexarotene, bortezomib, celecoxib, denileukin diftitox, erlotinib, estramustine, gefitinib, hydroxycarbamide, imatinib, pentostatin, masoprocol, mitotane, pegaspargase, and tretinoin. These chemotherapeutic agents may also be administered in combination.

In a sixth aspect, the present invention provides a method of screening a candidate therapeutic agent for use in treating ovarian cancer in a subject, the method comprising the step of assaying the candidate therapeutic agent for activity in decreasing the expression level of junction plakoglobin in the subject. As would be appreciated by a person skilled in the art, screening assays may be performed in vitro and/or in vivo.

In some embodiments, the method includes:

(a) administering the candidate therapeutic agent to the subject;

(b) detecting the expression level of junction plakoglobin in blood of the subject; and (c) comparing the expression level of junction plakoglobin in the blood of the subject with the expression level of junction plakoglobin in blood of an untreated subject having ovarian cancer, wherein if the expression level of junction plakoglobin in the subject is lower than the expression level of junction plakoglobin in the untreated subject, the candidate therapeutic agent is useful for treating ovarian cancer.

In a further embodiment of the sixth aspect of the invention, the method includes:

(a) detecting the expression level of junction plakoglobin in blood of a subject who has been administered the candidate therapeutic agent; and (b) comparing the expression level of junction plakoglobin in the blood of the subject with the expression level of junction plakoglobin in blood of an untreated subject having ovarian cancer, wherein if the expression level of junction plakoglobin in the subject is lower than the expression level of junction plakoglobin in the untreated subject, the candidate therapeutic agent is useful for treating ovarian cancer.

The expression level of junction plakoglobin can be assayed or detected in the subject using the methods described above. In some embodiments of the sixth aspect of the invention, the expression level of junction plakoglobin may be assayed or detected in a blood sample obtained from the subject. Examples of blood samples are as described above.

In a further aspect, prospective agents may be screened to identify candidate therapeutic agents for the treatment of ovarian cancer in a cell-based assay. In this regard, each prospective agent is incubated with cultured cells (for example cells obtained from an ovary of a normal subject or from a subject suffering from ovarian cancer, or cell lines derived from a normal or affected subject), and the expression level of junction plakoglobin is assessed.

Accordingly, in a seventh aspect the present invention provides a method of screening a candidate therapeutic agent for use in treating ovarian cancer in a subject, wherein the method comprises:

(a) exposing the candidate therapeutic agent to a cell expressing junction plakoglobin;

(b) measuring for a change in the expression level of junction plakoglobin in the cell; and (c) comparing the expression level of junction plakoglobin in the cell to a reference expression level for junction plakoglobin, wherein if the expression level of junction plakoglobin in the cell is lower than the reference expression level for junction plakoglobin, the candidate therapeutic agent is useful for treating ovarian cancer in a subject.

Reference herein to "lower" with respect to the sixth and seventh aspects of the invention is intended to mean an expression level of junction plakoglobin, whether at the translational (protein) or transcriptional (mRNA) stage, that is at least about 1%, 5%, 10%, 20%, 30%, 40%, 50%, 60%, 70%, 80%, 90%, 100%, 1.1-fold, 1.2-fold, 1.3-fold, 1.4-fold, 1.5-fold, 1.6-fold, 1.7-fold, 1.8-fold, 1.9-fold, 2-fold, 2.1-fold, 2.2-fold, 2.3-fold, 2.4-fold, 2.5-fold, 2.6-fold, 2.7-fold, 2.8-fold, 2.9-fold, 3-fold, 3.1-fold, 3.2-fold, 3.3-fold, 3.4-fold, 3.5-fold, 3.6-fold, 3.7-fold, 3.8-fold, 3.9-fold, 4-fold, 5-fold, 10-fold, 20 fold, 50-fold, 100-fold or greater, decreased compared to the expression level in the untreated subject.

The reference expression level for junction plakoglobin with respect to the sixth and seventh aspects of the invention may be determined as described above.

In another example, candidate therapeutic agents may be screened in organ culture-based assays. In this regard, each prospective agent is incubated with either a whole organ or a portion of an organ (such as a portion of an ovary of a normal or affected subject) derived from a non-human animal and modulation of the expression level of junction plakoglobin measured.

The present invention also enables compositions which can be used to perform any one or more of the aforementioned methods of the invention. Accordingly, in an eighth aspect the present invention provides a composition for detecting ovarian cancer in a subject, for identifying a subject having ovarian cancer, or for determining if a subject is susceptible to developing ovarian cancer, the composition including an agent that binds to, or interacts with, junction plakoglobin present in blood of the subject.

In one embodiment of the eighth aspect of the invention, the agent is an antibody specific for junction plakoglobin protein. Details regarding junction plakoglobin antibodies are provided above. In some embodiments, the composition further includes an agent that binds to, or interacts with, tumour associated antigen CA125. In some embodiments, the composition further includes an agent that binds to, or interacts with HE4.

In a ninth aspect, the present invention provides a kit for detecting ovarian cancer in a subject, for identifying a subject having ovarian cancer, or for determining if a subject is susceptible to developing ovarian cancer, the kit including means for detecting an expression level of junction plakoglobin in blood of the subject.

In one embodiment of the ninth aspect of the invention, the kit includes an agent that binds to, or interacts with, junction plakoglobin present in blood of the subject. In some embodiments, the agent is an antibody specific for junction plakoglobin protein. Details regarding junction plakoglobin antibodies are provided above. In some embodiments, the kit further includes means for detecting an expression level of tumour associated antigen CA125 in blood of the subject. In some embodiments, the kit further includes means for detecting an expression level of tumour associated antigen HE4 in blood of the subject.

In one embodiment of the ninth aspect of the invention, the kit includes a solid support, such as a chip, sensor, a microtiter plate or a bead or resin having a capture reagent attached thereon, wherein the capture reagent binds junction plakoglobin protein, and/or CA125 protein, and/or HE4 protein. Therefore, for example, the kits of the present invention can comprise antibodies specific for these proteins as the capture reagent, mass spectrometry probes for SELDI, such as ProteinChip® arrays, or a versatile fibre-based SPR sensing device. In the case of biospecific capture reagents, the kit can comprise a solid support with a reactive surface, and a container comprising the biospecific capture reagent.

In some embodiments of the ninth aspect of the invention, the kit can also include a washing solution or instructions for making a washing solution, in which the combination of the capture reagent and the washing solution allows capture of junction plakoglobin protein, and/or CA125 protein, and/or HE4 protein, on the solid support for subsequent detection by, for example, ELISA or mass spectrometry. The kit may include more than one type of adsorbent, each present on a different solid support.

In some embodiments, such a kit can include instructions for suitable operational parameters in the form of a label or separate insert. For example, the instructions may inform a consumer about how to collect the sample, how to wash the probe or the particular protein or proteins to be detected.

In some embodiments, the kit can include one or more containers with samples that represent a reference expression level for each protein, and are therefore to be used as standards for calibration.

In a tenth aspect, the present invention provides a biomarker of ovarian cancer, the biomarker being junction plakoglobin. As indicated above, junction plakoglobin serves as a biomarker of ovarian cancer given that the expression level of junction plakoglobin in the blood of a subject having ovarian cancer is higher than a reference expression level for junction plakoglobin (for example a subject that does not have ovarian cancer).

The inventors have identified junction plakoglobin as a biomarker indicative of ovarian cancer using a unique approach. Specifically, the inventors have analysed blood obtained directly downstream of a tumour (e.g. venous or arterial blood associated with a malignant tumour) to isolate and identify cancer-specific proteins secreted into the blood stream by the tumour. The inventors hypothesized that the concentration of such markers is higher in tumour blood when compared to their concentration in peripheral blood where such markers are diluted by the total blood volume.

Accordingly, in an eleventh aspect the present invention provides a method of identifying a biomarker for a cancer, the method comprising:

(a) obtaining a blood sample from a subject having the cancer, wherein the blood sample is obtained from venous or arterial blood associated with a malignant tumour;

(b) extracting the protein component of the blood sample;

(c) determining the level of expression of proteins present in the protein component of the blood sample; and (d) identifying a protein present in the protein component of the blood sample that has an expression level higher or lower than a reference expression level for the protein, wherein a protein present in the protein component of the blood sample that has an expression level higher or lower than a reference expression level for the protein is a biomarker for the cancer.

In the context of the eleventh aspect of the invention, reference to venous or arterial blood associated with a malignant tumour is taken to mean blood obtained directly downstream of the tumour. Such blood samples are typically obtained intraoperatively.

The protein component of the blood sample may be extracted using techniques well-known in the art. Techniques used will depend on whether the protein is extracted from whole blood, or from the serum or plasma component of blood. With respect to serum, techniques such as methanol extraction, Folch extraction, acetone extraction, acetonitrile extraction, or proteinase K protein depletion, may be employed (see Alshammari T M et al., 2015, *Saudi Pharmaceutical Journal*, 23: 689-697). Other techniques for extraction of protein from whole blood, plasma or serum may be employed such as ultrafiltration, dialysis, salting out, precipitation by isoelectric point, precipitation using polyethylene glycol (PEG) solid-phase extraction, and other techniques (see Lee C H, 2017, *Endocrinol. Metab. (Seoul)*, 32: 18-22; Callesen A K et al., 2009, *Proteomics*, 9: 1428-1441; and Feist P and Hummon A B, 2015, *Int. J. Mol. Sci.*, 16: 3537-3563).

Proteome analysis of biological samples for biomarker identification is challenged due to the dynamic range of protein expression in blood (>10 orders of magnitude). High-abundant proteins such as albumin in plasma can interfere with the detection of potential disease biomarkers which may have a much lower level of expression. To account for this, abundant proteins in the protein component of the blood sample can be depleted after extraction from the blood sample. Various protein depletion techniques can be employed such as those which deplete albumin using dye ligands in affinity chromatography columns (see Travis J and Pannell R, 1973, *Clin. Chim. Acta.*, 49: 49-52; Travis J et al., 1976, *Biochem. J.*, 157: 301-306) or by precipitation (see Fu Q et al., 2005, *Proteomics*, 5: 2656-2664; Colantonio D A et al., 2005, *Proteomics*, 5: 3831-3835; Chen Y Y et al., 2005, *Electrophoresis*, 26: 2117-2127; Warder S E et al., 2009, *Anal. Biochem.*, 387: 184-193). Other techniques include depletion of albumin in combination with IgG by coupling bacterial proteins, Protein A/G, to a solid support (see Fu Q et al., 2005, supra; Colantonio D A et al., 2005, supra; Fountoulakis M et al., 2004, *Amino Acids*, 27: 249-259). For the removal of multiple high-abundance proteins so as to enrich for low-molecular weight species (peptides/proteins) is use of centrifugal ultrafiltration (Tirumalai R S et al., 2003, *Mol. Cell Proteomics*, 2: 1096-1103; Orvisky E et al., 2006, *Proteomics*, 6: 2895-2902; Hood B L et al., 2005, *J. Am. Soc. Mass Spectrom.*, 16: 1221-1230; Bergen 3rd H R et al., 2003, *Dis. Markers*, 19: 239-249).

In some embodiments of the eleventh aspect of the invention, abundant proteins in the protein component of the blood sample are depleted by immunoaffinity depletion. In this regard, immunoaffinity columns using antibody-based approaches have been employed to remove multiple high-abundance proteins simultaneously. Examples of such immunoaffinity techniques are known in the art (see Pieper R et al., 2003, *Proteomics*, 3: 1345-1364; Huang L et al., 2005, *Proteomics*, 5: 3314-3328; Zolotarjova N et al., 2008, *J. Chromatogr.*, 1189: 332-338).

Commercially available depletion columns may also be used as described in Polaskova V et al., 2010, *Electrophoresis*, 31: 471-482. Such columns include Aurum Affi-Gel Blue mini kit (Bio-Rad, Hercules, CA, USA), Vivapure anti-HAS/IgG kit (Sartorius Stedim Biotech, Goettingen, Germany), Qproteome albumin/IgG depletion kit (Qiagen, Hilden, Germany), Multiple Affinity Removal Columns (MARC human-6) (Agilent Technologies, Santa Clara, CA, USA), Seppro Supermix LC2 column (Merck, KGaA, Darmstadt, Germany), and ProteoPrep 20 plasma immunodepletion kit (Sigma-Aldrich, St. Louis, MO, USA). Other immunoaffinity depletion columns may be used as preferred. In some embodiments, the Multiple Affinity Removal System (MARS) LC may be used (Agilent Technologies, Santa Clara, CA, USA). This column is known to remove the 14 most abundant proteins from serum.

In some embodiments, the level of expression of proteins present in the protein component of the blood sample is determined by two-dimensional difference gel electrophoresis. Two-dimensional difference gel electrophoresis (2-D DIGE) is a modified form of 2-D electrophoresis (2-DE) that allows one to compare two or three protein samples simultaneously on the same gel. The proteins in each sample are covalently tagged with different color fluorescent dyes that are designed to have no effect on the relative migration of proteins during electrophoresis. Proteins that are common to the samples appear as "spots" with a fixed ratio of fluorescent signals, whereas proteins that differ between the samples have different fluorescence ratios. With the appropriate imaging system, DIGE is capable of reliably detecting as little as 0.2 fmol of protein, and protein differences down to ±15%, over an approximately 10,000-fold protein concentration range. DIGE combined with digital image analysis therefore greatly improves the statistical assessment of proteome variation. Protocols for conducting 2-D DIGE are known in the art. Exemplary methods can be found in Sá-Correia I and Teixeira M C, 2010, *Expert Rev Proteomics*, 7: 943-953, and Pasquali M et al., 2017, *Methods Mol. Biol.*, 1654: 245-254. A summary of methods can be found in McNamara L E et al., 2010, *J R Soc. Interface*, 7 (Suppl 1): S107-S118.

In some embodiments, the two-dimensional difference gel electrophoresis is saturation labelling two-dimensional difference gel electrophoresis (see Arnold G J and Frohlich T, 2012, *Methods Mol. Biol.*, 854: 89-112). Saturation labelling 2-D DIGE uses Cy3 and Cy5 fluorophores with maleimide chemistry, and is used to label all cysteine residues within the extracted proteins. To ensure saturation is achieved, titration is required to find the optimal stoichiometry of the ratios of the reducing agent tris(2-carboxyethyl)phosphine (TCEP):protein:dye for the particular sample. This involves a qualitative assessment of the gels to determine which concentration results in the fewest artefacts in the resulting spot map. Saturation labelling greatly enhances sensitivity because all cysteines in a protein are labelled (rather than a small fraction of the lysine residues in minimal labelling 2-D DIGE).

Once the level of expression of proteins present in the protein component of the blood sample has been determined, a comparison is made to a reference expression level for each protein. The principal behind this has been described above. In this instance, the reference expression level may be derived from a level for each protein which is known to be found in blood from a subject not suffering from the cancer (i.e. a "normal" subject). For example, a reference expression level for each protein may be derived from blood of a normal subject, or may be derived from an average of the level of each protein in blood from a number of normal subjects (e.g. n=2 to 100 or more), wherein the subject or subjects have no prior history of the cancer. A reference expression level for each protein can also be obtained from one or more "normal" samples from a subject suspected to have, or which has, the cancer. For example, a reference expression level for each protein may be obtained from at least one peripheral vein blood sample (including a peripheral vein serum or plasma sample), and is preferably obtained from an average of peripheral vein blood samples (e.g. n=2 to 100 or more), wherein the subject or subjects are suspected of having, or which have, the cancer. Furthermore, a reference expression level for each protein may be a level of each protein that is present in blood from a subject having a benign tumour. In this instance, the reference expression level for each protein would be derived from blood of a subject having at least one benign tumour, or may be derived from an average of the level of each protein in a number of benign tumours from the same or different subjects (e.g. n=2 to 100 or more). The reference expression level for each protein present in the protein component of the normal sample may be determined using the methods described above, including the use of saturation labelling two-dimensional difference gel electrophoresis.

In some embodiments of the eleventh aspect of the invention, a protein which is differentially expressed between the blood sample of the subject and a normal sample, is a potential biomarker for the cancer. In other words, a protein present in the protein component of the blood sample that has an expression level higher or lower than a reference expression level for the protein is a biomarker for the cancer.

With respect to the eleventh aspect of the invention, reference herein to "higher" with respect to the expression level of a protein, whether at the translational (protein) or transcriptional (mRNA) stage, is intended to mean, for example, at least about a 1%, 5%, 10%, 20%, 30%, 40%, 50%, 60%, 70%, 80%, 90%, 100%, 1.1-fold, 1.2-fold, 1.3-fold, 1.4-fold, 1.5-fold, 1.6-fold, 1.7-fold, 1.8-fold, 1.9-fold, 2-fold, 2.1-fold, 2.2-fold, 2.3-fold, 2.4-fold, 2.5-fold, 2.6-fold, 2.7-fold, 2.8-fold, 2.9-fold, 3-fold, 3.1-fold, 3.2-fold, 3.3-fold, 3.4-fold, 3.5-fold, 3.6-fold, 3.7-fold, 3.8-fold, 3.9-fold, 4-fold, 5-fold, 10-fold, 20 fold, 50-fold, 100-fold increase in the expression level of the protein compared to the reference expression level for the protein.

With respect to the eleventh aspect of the invention, reference herein to "lower" with respect to the expression level of a protein, whether at the translational (protein) or transcriptional (mRNA) stage, is intended to mean, for example, at least about a 1%, 5%, 10%, 20%, 30%, 40%, 50%, 60%, 70%, 80%, 90%, 100%, 1.1-fold, 1.2-fold, 1.3-fold, 1.4-fold, 1.5-fold, 1.6-fold, 1.7-fold, 1.8-fold, 1.9-fold, 2-fold, 2.1-fold, 2.2-fold, 2.3-fold, 2.4-fold, 2.5-fold, 2.6-fold, 2.7-fold, 2.8-fold, 2.9-fold, 3-fold, 3.1-fold, 3.2-fold, 3.3-fold, 3.4-fold, 3.5-fold, 3.6-fold, 3.7-fold, 3.8-fold, 3.9-fold, 4-fold, 5-fold, 10-fold, 20 fold, 50-fold, 100-fold decrease in the expression level of the protein compared to the reference expression level for the protein.

Determining the identity of a protein which is differentially expressed between the subject sample and control sample can be achieved using methods known in the art. One such method is through the use of mass spectroscopy. Exemplary methods have been described above. In some embodiments, liquid chromatography coupled to tandem mass spectrometry (LC-MS/MS) may be employed. In this manner, acquired MS data can be converted to a format searchable against protein databases. For example, conversion of MS data to a Mascot generic format according to Chambers M C et al., 2012, *Nature Biotechnology*, 30: 918, and searching against the SwissProt human database as per Perkins D N et al., 1999, *ELECTROPHORESIS*, 20: 3551-3567).

In some embodiments of the eleventh aspect of the invention, the cancer is ovarian cancer as described in detail above. In some embodiments, the blood sample of the subject to be tested is an ovarian blood sample. In some embodiments, the ovarian blood sample is obtained from ovarian venous or arterial blood, i.e. blood associated with an ovarian tumour of the cancer. The ovarian vein carries deoxygenated blood from its corresponding ovary to inferior vena cava or one of its tributaries. The ovarian vein is located in the suspensory ligament of the ovary. Ovarian venous blood is separate and distinct from blood of a vein from a peripheral part of the body (i.e. peripheral blood).

The invention is further illustrated in the following example. The example is for the purpose of describing particular embodiments only and is not intended to be limiting with respect to the above description.

EXAMPLE

Identification of Junction Plakoglobin as a
Biomarker for Ovarian Cancer

Early detection of ovarian cancer is the most effective means to improve ovarian cancer survival. However, a diagnostic test for early ovarian cancer remains elusive and population screening is therefore not possible. The inventors recognized that proteins which are over-expressed by cancer cells and then released into the bloodstream are ideal markers for early detection of ovarian cancer. However, a major "quantitative" challenge of ovarian cancer biomarker research is to identify the cancer at an early stage when it is small and the amount of cancer-specific proteins secreted into the blood stream is extremely low. To overcome this difficulty the inventors hypothesized that protein markers are more highly concentrated in ovarian venous blood directly downstream of an ovarian tumour compared to peripheral blood which has been taken from the cubital vein where the marker is diluted in the total blood volume.

Another significant "qualitative" problem of biomarker detection is how to identify circulating cancer-specific proteins given that they are commonly masked by high abundant proteins. For example, in blood the dynamic range of protein abundance covers more than 10 orders of magnitude and is beyond detection and quantification limits of explorative proteomic approaches. This obstacle can partially be overcome by depletion of high abundant proteins which yields a 2-4 fold increase in protein identification when compared to non-depleted samples. However, relevant tumour proteins might still be below the detection limit and therefore missed by common proteomics approaches.

In recognition of the limitations listed above, in order to identify biomarkers indicative of ovarian cancer, the present study analyzed the serum proteome of ovarian blood obtained from ovaries with stage I epithelial ovarian carcinomas. The analysis employed a combination of saturation labelling two-dimensional difference gel electrophoresis (2D DIGE) and tandem mass spectrometry.

Material and Methods
Patient Samples

Blood from ovarian and peripheral (cubital) veins was collected intraoperatively with patient consent and approval by the Research Ethics Committee at the Royal Adelaide Hospital, Adelaide, South Australia. Ovarian blood samples from 6 patients with stage Ia ovarian cancer (2 serous papillary and 4 endometrioid adenocarcinomas), 2 patients with functional ovarian cysts and 4 patients with benign serous cystadenomas were used for biomarker discovery. Ovarian and peripheral blood was collected into clotting tubes (Greiner Bio-one, Austria), serum or plasma EDTA prepared by centrifugation at 3,000 rpm for 15 min at room temperature and supernatant was stored at −80° C.

For the confirmation and validation phase peripheral blood samples of 89 patients with early stage ovarian cancer, 38 patients with late stage ovarian cancer and 98 normal controls were sourced from various biobanks (Table 1).

Non-ovarian cancer samples (early stage breast (n=12)) were obtained from the Precision Med Inc, Solana Beach, California, USA and Conversant Biosciences Inc, Huntsville, Alabama, USA.

Depletion of Top 14 Abundant Serum Proteins

The 14 most abundant serum proteins were depleted using the multiple affinity removal system (MARS) LC (Agilent, Santa Clara, California, USA) according to the manufacturer's recommendations. In brief, 100 µl serum was mixed with 297 µl buffer A (Agilent) and 3 µl protease inhibitor cocktail (Sigma-Aldrich, St. Louis, Missouri, USA), then filtered through a 0.22 µm spin filter (Corning, New York, USA) using a centrifuge at 16,000×g at room temperature for 1 min. Depletion of 160 µl of the filtrate was carried out on an Agilent 1100 HPLC using a 4.6×100 mm MARS human 14 depletion column (Agilent). Low abundant protein fraction was collected and mixed 1:5 with 100% (v/v) acetone (ice-cold) and stored at −20° C. until further use. Proteins were pelleted by centrifugation for 45 min at 12,000×g and −9° C. The protein pellet was washed in 3 mL ice-cold 100% (v/v) acetone, lia), 1% (v/v) protease inhibitor cocktail (Sigma), 1.1% (v/v) PSC protector reagent (Roche), pH 7.5). The suspended protein samples were desalted via a 10 kDa cut-off spin filter (Vivacon 500, Sartorius, Gottingen, Germany) by centrifugation for 30 min at 14,000×g, 15° C. The filter was washed five times by adding 400 µl of TUC4% and centrifugation for 30 min at 14,000×g, 15° C. The protein concentration of resulting protein sample was measured using an EZQ™ protein quantification kit (Life Technologies, Carlsbad, California, USA) according to the manufacturer's manual.

Saturation Labelling Two-Dimensional Difference Gel Electrophoresis (2D DIGE)

Before saturation labelling, the protein samples were tested for consistent depletion by sodium dodecyl sulfate polyacrylamide gel electrophoresis (SDS-PAGE) and proteins were visualized by silver stain (FIG. 1). Amount of protein labels S-200 and S-300 (NH DyeAgnostics GmbH, Halle (Saale), Germany) and reduction agent Tris(2-carboxyethyl)phosphine hydrochloride (TCEP) (NH DyeAgnostics) was optimized according to the manufacturer's recommendation and protocols (Arnold G J and Frohlich T, 2012, "2D DIGE saturation labeling for minute sample amounts, *Methods in Molecular Biology* (Clifton, NJ), 854: 89-112) with 1.5 µl of the TCEP (resuspended in 400 µl of H$_2$O) and 3 µl of the respective label (S-200 and S-300) chosen for the subsequent saturation DIGE experiment.

Six serum samples from the venous flow of malignant stage I epithelial ovarian tumors, 6 peripheral serum samples from the same patients, 6 serum samples from the venous flow of benign ovarian tumors, and one internal pooled standard (IPS) were labelled. For this, 5 µg of total proteins from the depleted serum collected from the ovarian venous flow and matched peripheral serum were labelled with S-200. The IPS, consisting of an equal mixture of 5.9 µg of total proteins from each sample, was labelled with S-300. The volume of each protein sample was equalized to 9 µl using TUC4%, then proteins were reduced for 1 h at 35° C. in the dark using 1.5 µl TCEP for the samples. IPS was

TABLE 1

|  |  |  | Validation | | International set | | Ovarian cancer subtypes | | Breast cancer | |
| --- | --- | --- | --- | --- | --- | --- | --- | --- | --- | --- |
| Group | Class | Stage | No | Age | No | Age | No | Age | No | Age |
| High grade | Early | I | 13 | 60 (43-84) | 20 | 60 (38-86) |  |  |  |  |
| serous |  | II |  |  | 17 | 60 (40-78) |  |  |  |  |
|  | Late | III |  |  | 24 | 71 (47-84) |  |  |  |  |
|  |  | NA |  |  | 15 | 64 (39-80) |  |  |  |  |
| Endometrioid | Early | I |  |  |  |  | 16 | 57 (33-90) |  |  |
| Mucinous | Early | I |  |  |  |  | 12 | 58 (37-72) |  |  |
| Clear cell | Early | I |  |  |  |  | 11 | 61 (43-82) |  |  |
| Breast cancer | Early | I, II |  |  |  |  |  |  | 8 | 56 (41-68) |
|  | Late | III, IV |  |  |  |  |  |  | 4 | 76 (75-84) |
| Control | — | — | 16 | 59 (43-83) | 37 | 46 (28-79) | 38 | 47 (26-79) | 7 | 60 (37-72) |

Descriptive statistics of patient samples used for all ELISAs

Age is given as median with the range in brackets. In case of ovarian cancer, stage in given as FIGO stage.

stored at −20° C. for one hour then centrifuged for 45 min at 12,000×g and −9° C. Supernatant was discarded and the protein pellet was air-dried for 10 min to remove residual acetone.

Proteins were suspended in 400 µl TUC4% (7 M urea (Merck, Darmstadt, Germany), 2M thiourea (GE Healthcare, Little Chalfont, UK), 4% (w/v) 3-[(3-cholamidopropyl)dimethylammonio]-1-propanesulfonate (CHAPS) (Roche, Basel, Switzerland), 30 mM tris(hydroxymethyl) aminomethane (Tris) (Astral Scientific, Taren Point, Austradiluted with TUC4% to a concentration of 0.56 µg/µl, subsequently 31.9 µl TCEP was added and incubated at 35° C. for 1 h in the dark. After reduction, the proteins were labelled using 3 µl of S-200, the IPS was labelled using 63.7 µl of S-300 and incubated for 1 h at 35° C. in the dark. For each sample, the reaction was quenched by adding 13.5 µl (IPS: 286.7 µl) of TUC4% supplemented with 2% (w/v) DTT (Roche) and 4% (v/v) Pharmalyte 3-10 (GE Healthcare).

2D PAGE

Eighteen 24 cm immobilized pH gradient (IPG) strips with a pH range of 3-10 NL (Bio-rad, Hercules, California, USA) were rehydrated in 500 µl of TUC1% (6 M urea (Merck), 2 M thiourea (GE Healthcare), 1.2% (v/v) 2,2 Dithiodiethanol (Sigma-Aldrich), 0.5% (v/v) Pharmalyte 3-10 (GE Healthcare)) overnight at room temperature, then stored at −80° C. until further use. 5 µg of protein sample mixed with 5 µg IPS was loaded via anodal cup-loading. Isoelectric focusing (IEF) was carried out using an IPGPhor II (GE Healthcare) with the following settings: 150 V for 1 h, 300 V for 1 h, 600 V for 1.5 h, increase to 8000 V by gradient over 2 h, 24.000 Vh at 8000V, under exclusion of light. Current was limited to 50 µA per IPG strip. After IEF, IPG strips were stored at −80° C. until further use.

Before SDS-PAGE, IPG strips were equilibrated in Equilibration Buffer (Serva) with urea (Merck) added to a final concentration of 6 M for a total of 2×15 min. SDS-PAGE was carried out on a HPE Tower (Serva, Heidelberg, Germany) using 20×25 cm² gels with a T-value of 12.5% attached to a non-fluorescent backing foil (Serva). The following limiting settings were applied for electrophoresis: 30 min 100 V and 7 mA/gel, 30 min 200 V and 13 mA/gel, 10 min 300 V and 20 mA/gel, removal of IPG strip, 3 hours 50 min at 1500 V and 40 mA/gel.

Image Acquisition

After SDS-PAGE, gels were scanned using a Typhoon Trio Imager (GE Healthcare). S-200 channel was scanned with a photomultiplier tension (PMT) of 600 V, an emission window of 580 nm BP30, excitation using a green laser (532 nm). S-300 was scanned with a PMT of 600 V, an emission window 670 nm BP30 and excitation with a red laser (633 nm).

DIGE Data Analysis

Before spot detection, acquired images were warped using Robust Automated Image Normalization (RAIN) (Dowsey A W et al., 2006, "Examination of 2-DE in the Human Proteome Organisation Brain Proteome Project pilot studies with the new RAIN gel matching technique", *Proteomics*, 6: 5030-5047; and Dowsey A W et al., 2008, wards the spot volumes were re-normalized. The number of detected spots per gel is shown in Table 2. Normalized spot volumes were exported using the DeCyder XML toolbox (GE Healthcare). Data was analyzed using R (version 3.2.2, The R Foundation for Statistical Computing) (R Core Team. R: A Language and Environment for Statistical Computing Vienna, Austria, 2013). Statistical testing was carried out by t-tests.

Liquid Chromatography Tandem Mass Spectrometry (LC-MS/MS)

Figure 2:
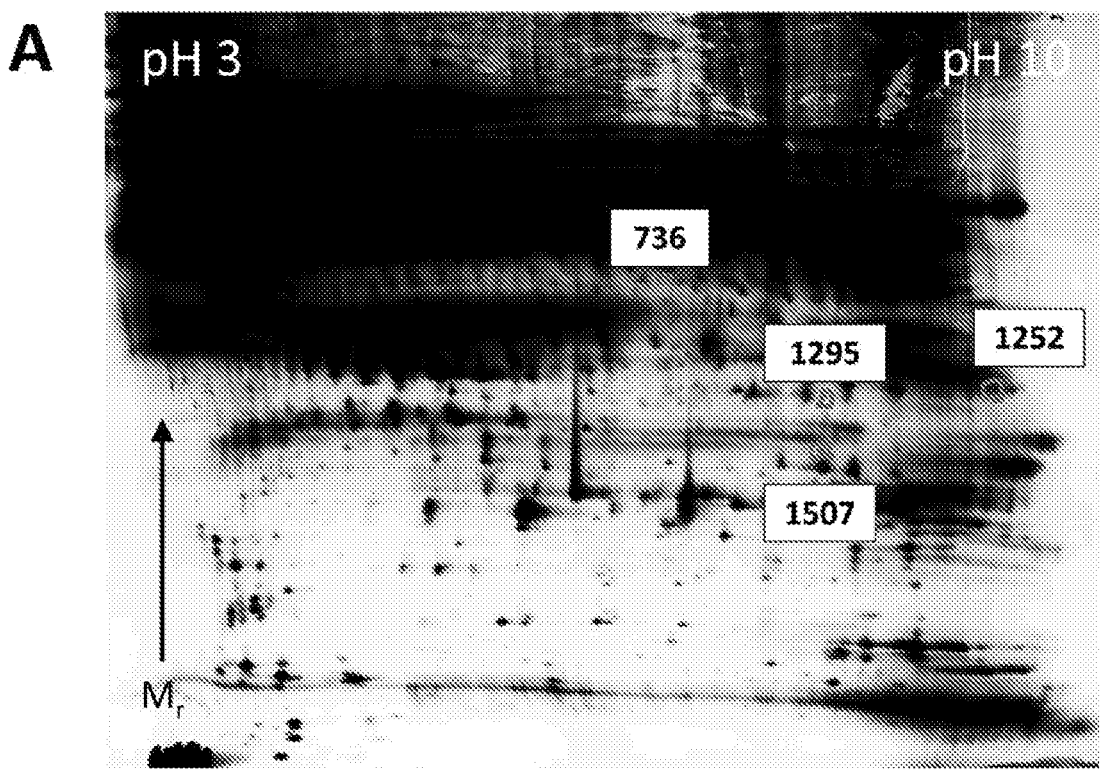
FIG. 2—A DIGE image and boxplots of protein spot abundance following ovarian blood MARS treatment and 2D DIGE analysis. (A) Representative, contrast-adjusted DIGE image of depleted blood serum. Numbers indicate spots of higher abundance in ovarian versus peripheral blood from early stage ovarian cancer patients and ovarian blood from patients with benign ovarian lesions. (B) Boxplots of spot abundance across the analysed DIGE gels. Samples: CO—Cancer ovarian serum, CP—Cancer peripheral serum and BO—Benign ovarian serum. All p-values between CO vs CP and CO vs. BO<0.05. Junction plakoglobin (JUP) was identified in all spots.
Figure 2:
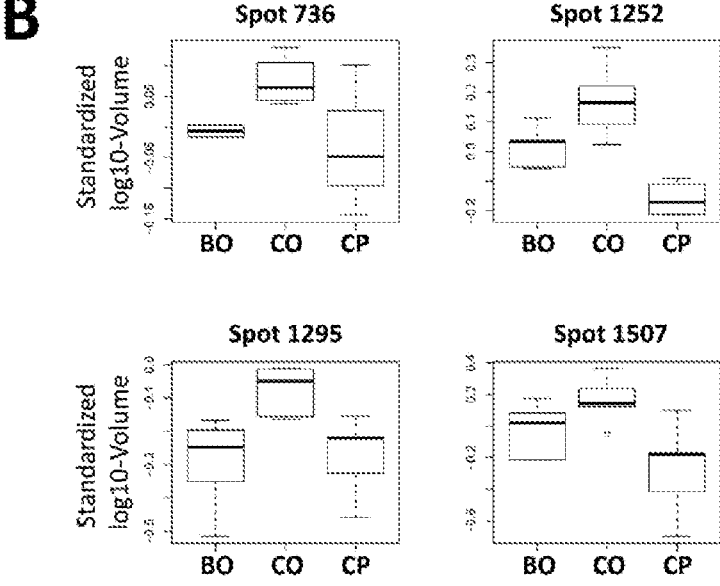

Primary candidate spots (736, 1252, 1295, 15017, see FIG. 2) were excised from eight gels using Ettan™ Spot-Picker (GE Healthcare) and the respective spots were combined. Proteins were digested using Trypsin (Promega, Madison, Wisconsin, USA). Tryptic peptides were dried using a SpeedVac (Thermo-Fisher, Waltham, Massachusetts, USA) and suspended in 12 µl of FA2 (2% (v/v) acetonitrile (Merck), 0.1% (v/v) formic acid (Sigma-Aldrich)). LC-MS/MS was carried out using an Ultimate 3000 RSLC system (Thermo-Fisher Scientific) connected to an Impact HD™ Q-TOF mass spectrometer (Bruker Daltonics, Bremen, Germany) via an Advance CaptiveSpray source (Bruker Daltonik). Ten microliters of digested peptides were injected and pre-concentrated onto a C18 trapping column (Acclaim PepMap100, 75 µm (ID)×2 cm, Thermo-Fisher Scientific) at a flow rate of 5 µl/min 2% (v/v) acetonitrile, 0.1% (v/v) trifluoroacetic acid for 10 min. Subsequently, peptides were separated using a 75 µm (ID)×50 cm C18 column (Acclaim PepMap100, Thermo-Fisher Scientific) at a flow rate of 0.3 µL/min using a binary buffer system and a linear gradient from 5% to 45% Buffer B (Buffer A (5% (v/v) acetonitrile (Merck), 0.1% (v/v) formic acid (Sigma-Aldrich)), Buffer B (80% (v/v) acetonitrile (Merck), 0.1% (v/v) formic acid (Sigma-Aldrich)) over 70 min, followed by a 20 min wash with 90% B and a column re-equilibration with 5% B for 20 min. Precursor ions were selected for MS/MS of the mass range of 300-2,000 m/z using the data-dependent Bruker's Shotgun Instant Expertise™ acquisition method. Analyzed precursor ions were excluded from re-analysis unless their intensity increased by a factor of 5. Singly charged precursor ions were excluded from

TABLE 2

| | | | | | | Combined ions score | Significant unique sequences | Coverage [%] | emPAI |
|---|---|---|---|---|---|---|---|---|---|
| | | | JUP identified by Mascot in the spots of primary interest | | | | | | |
| Spot | UniProt Accession | UniProt Name | Description | MW | pI | | | | |
| 736 | P14923 | PLAK_HUMAN | Junction plakoglobin | 81,693 | 5.75 | 226 | 3 | 7.2 | 0.12 |
| 1252 | P14923 | PLAK_HUMAN | Junction plakoglobin | 81,693 | 5.75 | 49 | 2 | 11.4 | 0.08 |
| 1295 | P14923 | PLAK_HUMAN | Junction plakoglobin | 81,693 | 5.75 | 58 | 3 | 8.3 | 0.12 |
| 1507 | P14923 | PLAK_HUMAN | Junction plakoglobin | 81,693 | 5.75 | 144 | 2 | 5.4 | 0.08 |

MW: Molecular weight in Dalton, pI: Isoelectric point.
Coverage: Percentage of protein sequence covered by identified peptides.
emPAI: exponentially modified protein abundance index "Automated image alignment for 2D gel electrophoresis in a high-throughput proteomics pipeline", *Bioinformatics* (Oxford, England), 24: 950-95) applying the recommended standard settings. All gels were aligned to the IPS (S-300 channel) of Gel01.

Protein spot detection was carried out using DeCyder 7.0 (GE Healthcare). In brief, expected number of spots for detection was set to 8000, afterwards an area of interest was defined and spots within this area were excluded based on their slope (>2) and their area (<450). Areas of the gel exhibiting saturated parts were excluded by hand and after-acquisition. Collision energy was dynamically set between 23% and 65%, depending on the m/z of the precursor ion.

Protein Identification

Acquired MS data was converted to Mascot generic format using ProteoWizard version 3.0.11768 (Chambers M C et al., 2012, "A cross-platform toolkit for mass spectrometry and proteomics", *Nature Biotechnology*, 30: 918) and searched against the SwissProt human database (downloaded 17 Aug. 2018; 20,387 entries) using Mascot (Version 2.4.1) (Perkins D N et al., 1999, "Probability-based protein identification by searching sequence databases using mass spectrometry data", *ELECTROPHORESIS*, 20: 3551-3567). Precursor mass tolerance was set to 20 ppm, fragment mass tolerance to 0.2 Da. Variable modifications of oxidation of methionine and N-acetylation of protein N-terminal and no fixed modifications were specified, with the digestion enzyme specified as trypsin omitting the proline rule. Percolator cut-off of 1% was used for peptides, only proteins with at least two significant unique peptide identification were considered.

Enzyme-Linked Immunosorbent Assay (ELISA)

Junction Plakoglobin (JUP) ELISA kits were purchased from MyBiosource, San Diego, California, USA. ELISAs were performed according to the manufacturer's protocol with the modification of using 300 µl wash solution (instead of 350 µl) between steps. Plate design was randomized using R. Serum samples for JUP ELISA were diluted 1:10 in 1×PBS pH 7.4. ELISA plates were developed for 15 min, afterwards absorbance at 450 nm was measured using a Biotrak II Reader (GE Healthcare). A standard curve was constructed by averaging (arithmetic mean) the respective absorbance and subtracting the blank. Using R, a regression curve was fitted through a log-log diagram of absorbance versus concentrations of the standards for each ELISA plate and used to calculate the JUP concentration of the samples. Difference in mean between groups was tested using a two-sided t-test, significance level was set at $\alpha=0.05$. All Correlations were calculated using a Spearman rank correlation.

CA125 Measurements

The concentration of CA125 was measured by SA Pathology (Adelaide, Australia).

Results

Research Strategy

In the discovery phase of the project the proteome of a) ovarian and peripheral blood from the same early ovarian cancer patient were compared to identify concentration differences indicating an ovarian origin of a potential marker protein, and b) ovarian blood from ovarian cancers and benign ovarian lesions were compared to exclude protein expression changes caused by the ovarian blood sampling process. Elevated JUP serum levels were confirmed by ELISA comparing the peripheral blood of a small cohort of ovarian cancer patients versus normal controls and finally validated with an independent large multicenter international cohort of cancer patients and controls.

JUP Discovery

Serum Depletion

The quality of serum depletion was assessed using SDS-PAGE and deemed satisfactory (FIG. 1).

Saturation 2D DIGE

Figure 3:
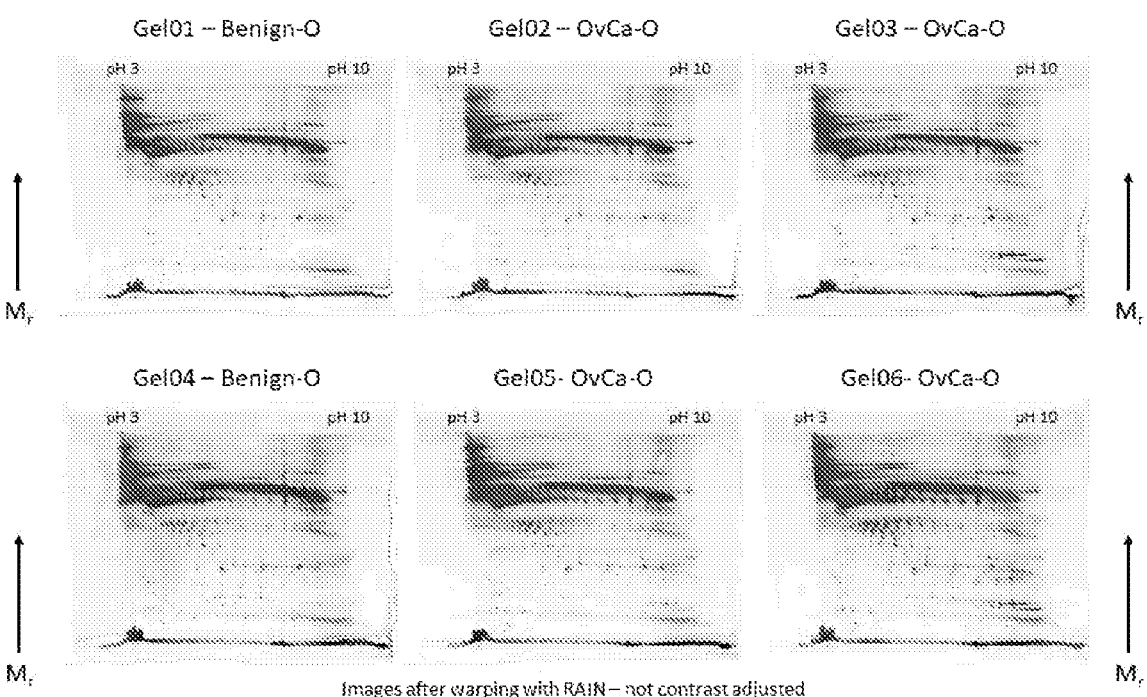
FIG. 3—DIGE gels prepared from the depleted blood serum of individual patients, IPG 3-10NL, 24 cm, 5 µg protein load, SDS-PAGE: T=12.5%. Images show the non-contrast adjusted S-200 channel after warping using the RAIN algorithm. Samples: Benign-O—Serum from benign ovarian tumour; OvCa-O—Serum from ovarian cancer; OvCa-P—Peripheral serum from patient with ovarian cancer.
Figure 3:
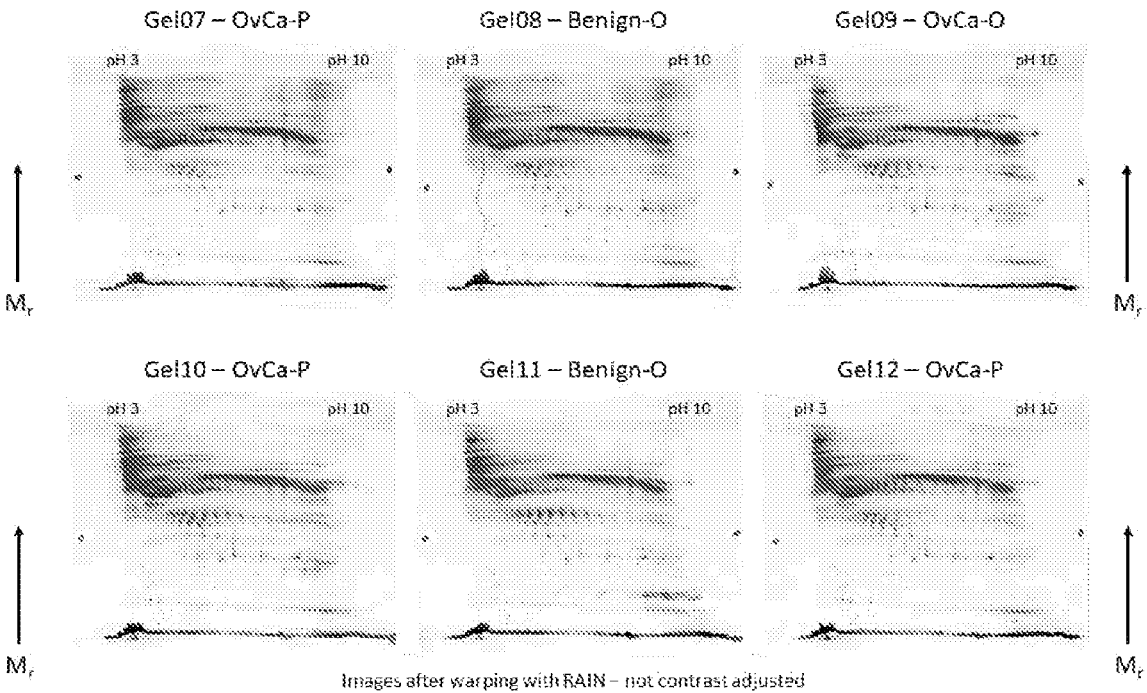
Figure 3:
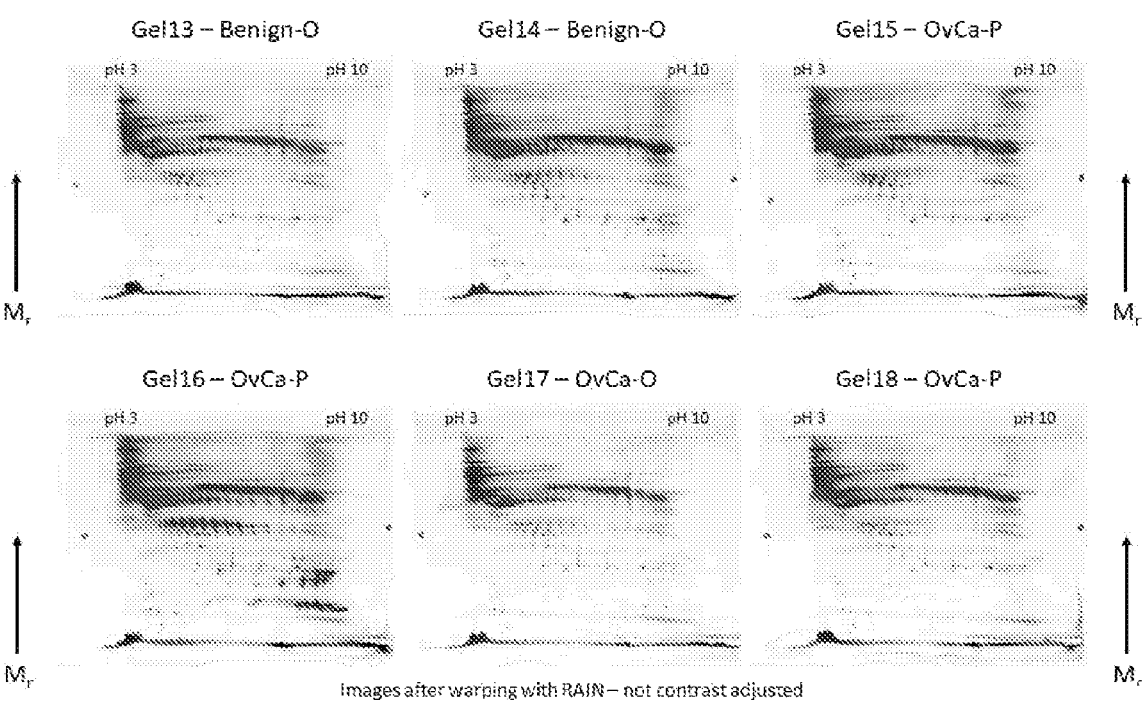

Acquired images were warped using RAIN (FIG. 3). Subsequently, protein spots were detected using DeCyder and saturated areas were excluded by hand. The number of detected protein spots on each gel is shown in Table 3. Normalized spot volumes were exported using DeCyder XML toolbox, standardized against the spot volume of the corresponding spot in the IPS (S-300) channel and log 10 transformed. Our first hypothesis was that proteins which are of higher abundance in venous flow from a malignant ovarian tumor (ovarian serum) compared with their abundance in peripheral serum are potential markers for early stage ovarian cancer. For this, a paired, one-sided t-test was applied. Protein spot volume data exhibiting a p-value <0.05 and positive fold-change was regarded of significantly higher abundance. Potential increase of abundance of protein spot volumes was controlled by using a second t-test, incorporating a group of ovarian serum from patients with a benign ovarian tumor. We hypothesized that potential markers for early stage ovarian cancers are of higher abundance in ovarian serum from malignant tumors than in the ovarian serum from benign tumors. For this a one-sided t-test was applied. In summary, proteins of higher abundance in: (i) ovarian serum compared with peripheral serum; and (ii) in ovarian serum from malignant tumor compared with ovarian serum from benign tumors, were regarded as primary candidates for biomarkers of early stage ovarian cancer. Out of a total of 2,692 spots tested, four spots satisfied the outlined criteria (spots 736, 1252, 1295 and 1507, see FIG. 2 and Table 2) and were subjected to identification by LC-MS/MS.

LC-MS/MS Protein Identification

Mass spectrometry found JUP to be present in 4 out of 4 analyzed spots (Table 2) and so JUP was chosen for further analysis by ELISA.

TABLE 3

| Gel | Experimental Group | Number of detected spots |
|---|---|---|
| Gel01 | Benign-O | 2,504 |
| Gel02 | OvCa-O | 2,474 |
| Gel03 | OvCa-O | 2,493 |
| Gel04 | Benign-O | 2,208 |
| Gel05 | OvCa-O | 2,352 |
| Gel06 | OvCa-O | 2,428 |
| Gel07 | OvCa-P | 2,325 |
| Gel08 | Benign-O | 2,375 |
| Gel09 | OvCa-O | 2,715 |
| Gel10 | OvCa-P | 2,364 |
| Gel11 | Benign-O | 2,174 |
| Gel12 | OvCa-P | 2,244 |
| Gel13 | Benign-O | 2,285 |
| Gel14 | Benign-O | 2,200 |
| Gel15 | OvCa-P | 2,406 |
| Gel16 | OvCa-P | 2,359 |
| Gel17 | OvCa-O | 2,279 |
| Gel18 | OvCa-P | 2,278 |

JUP Confirmation

Figure 4:
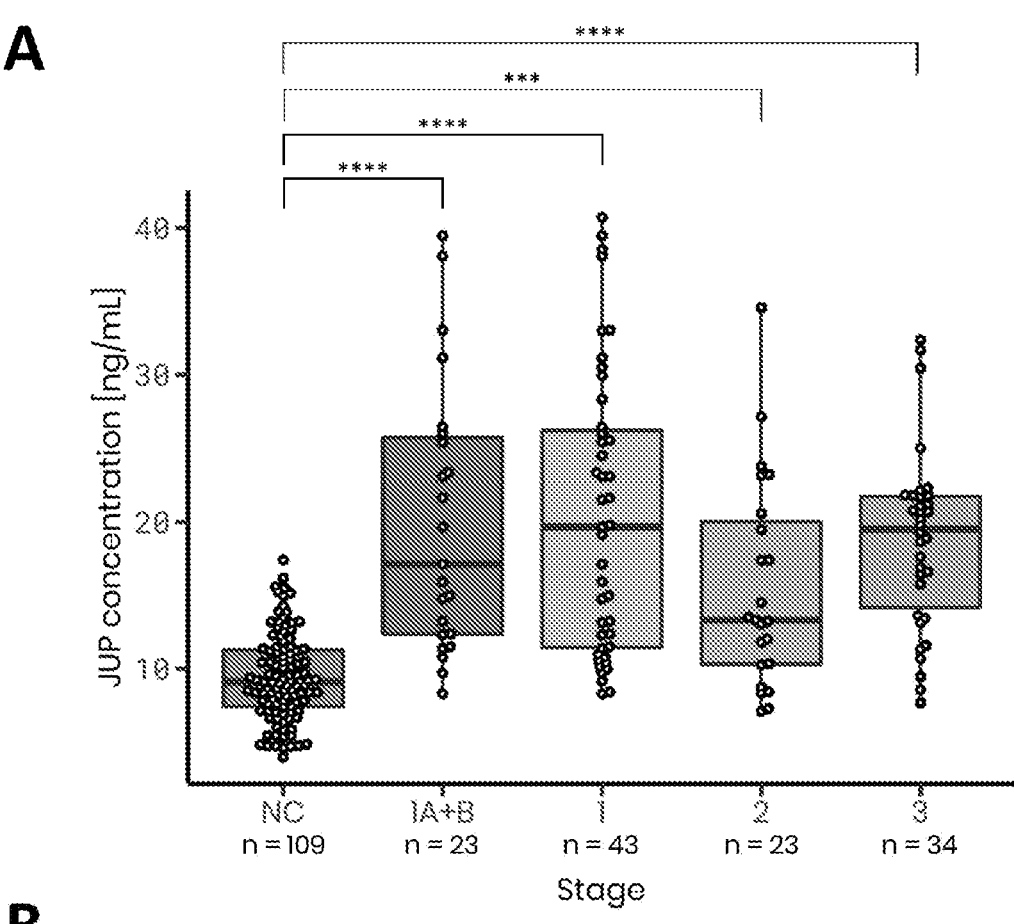
FIG. 4—Graphs showing multicentre validation of junction plakoglobin (JUP). (A): Normal controls (NC) plasma samples, stage 1A+B, stage 1 and in advanced stages 2 and 3 serous epithelial ovarian cancer plasma samples. Samples were measured using ELISA and a t-test was applied. NC vs. Stage 1A+B (2.12 fold change; p=1.00E-05; n=23); vs. Stage 1 (2.17 fold change; p=3.00E-09; n=43) and advanced stages 2 (1.66 fold change; p=4.40E-04; n=23) and stage 3 (1.98 fold change; p=2.00E-10; n=34) (B) ROC analysis of JUP (orange), CA125 (yellow) and logistic regression model combining JUP+CA125 (blue). AUC values were calculated as follows: Stage 1A+B: JUP: 0.895; CA125: 0.906; JUP+CA125: 0.943; Stage 1: JUP: 0.876; CA125: 0.945; JUP+CA125: 0.965.
Figure 4:
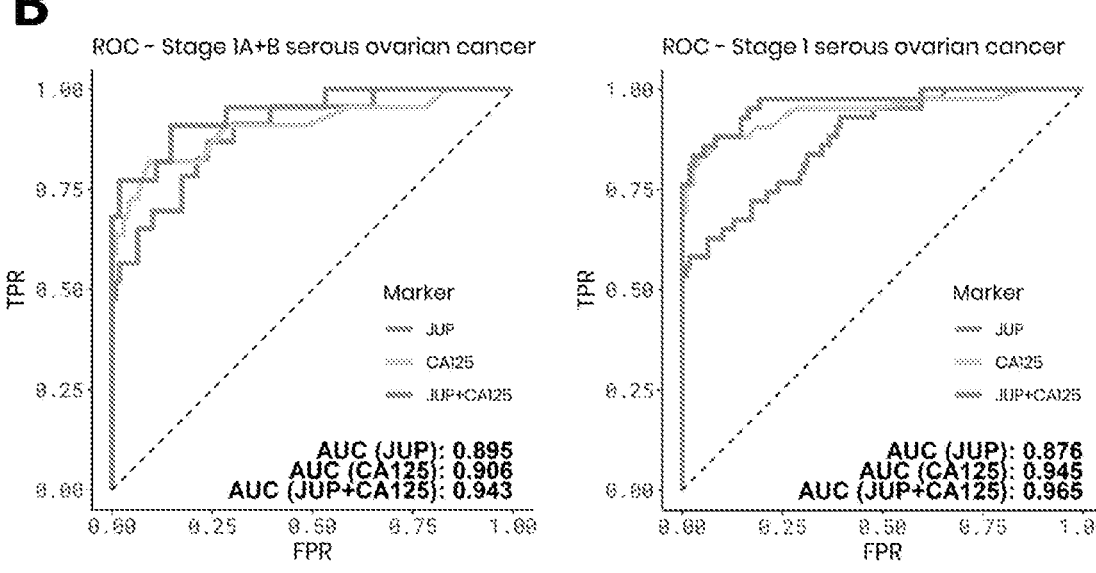

JUP serum levels were assessed in a small cohort of early stage ovarian cancer samples (n=13) and normal controls (n=16) by ELISA. JUP serum levels were found to be significantly elevated in the cancer cohort (p=0.05) (FIG. 4A).

JUP Validation

JUP plasma levels were validated by means of an international multicentre cohort. Plasma JUP levels were significantly higher in early stage (n=37, 1.89 fold increase, p<0.001) and late stage (n=38, 1.96 fold increase, p<0.001) versus normal controls (n=37) (t-Test) (FIG. 4B). Receiver operator characteristics (ROC) resulted in an area under the curve (AUC) of 0.79 for early stage high grade serous ovarian cancer versus normal controls (FIG. 4C) and two maxima (BM=0.46) with a sensitivity of 86.4%/51.3% and a specificity of 59.5%/94.6%, respectively (Bookmaker informedness).

Figure 5:
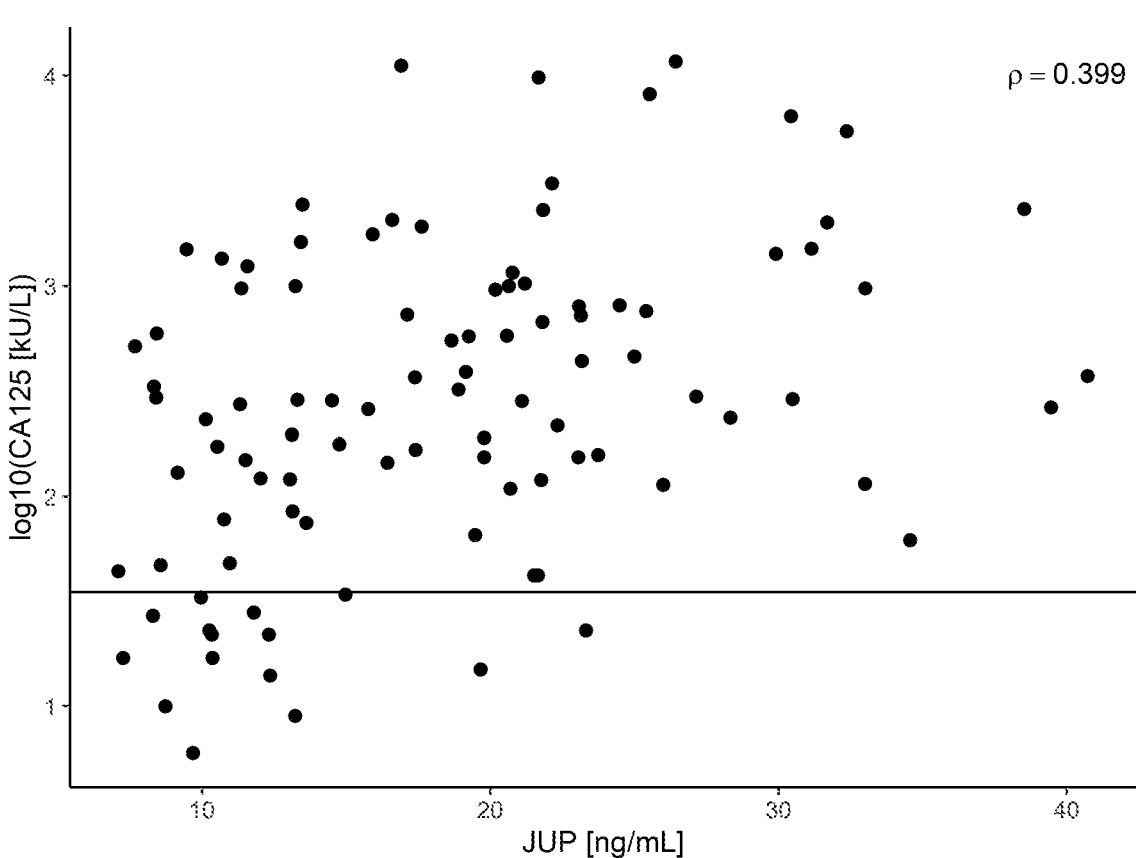
FIG. 5—Scatterplot of JUP and CA125 plasma concentrations in all measured serous ovarian cancer patients. Line depicting the logo of a CA125 concentration of 35 kU/L. Spearman correlation ρ=0.39.

JUP and CA125 plasma concentrations showed weak correlation (p=0.22, Spearman's rank test) (FIG. 5). A Logistic regression model combining JUP and CA125 for the classification of early stage ovarian cancer patients and normal controls was calculated using R. ROC of the resulting model were calculated, exhibiting an AUC of 0.95 for early stage ovarian cancer. However, in this dataset the singular use of CA125 concentration already exhibits an AUC of 0.95, therefore the combination of CA125 and JUP did not improve the classification in our dataset (data not shown).

JUP in Non-Serous Epithelial Ovarian Cancer Subtypes

Figure 6:
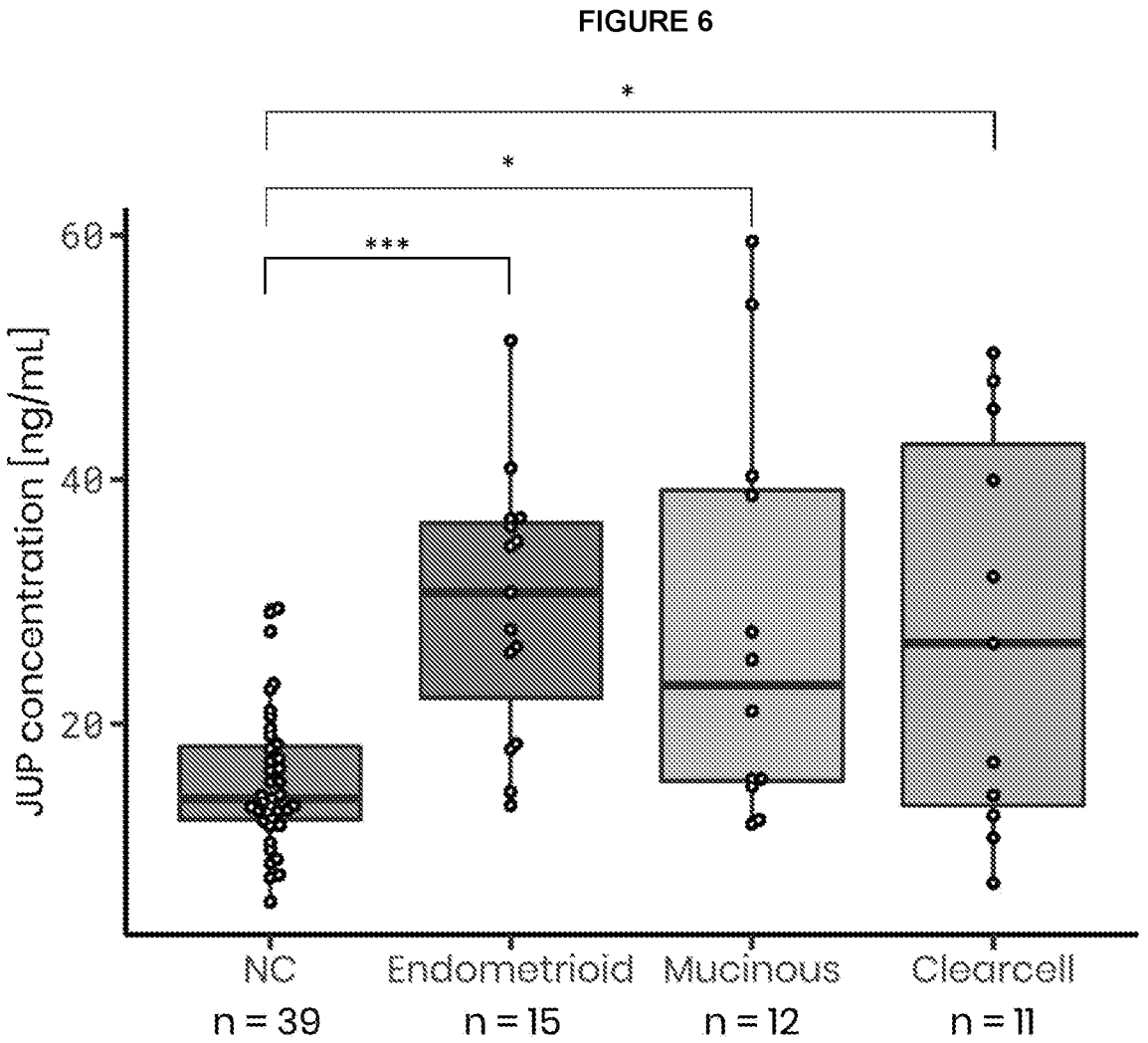
FIG. 6—a graph showing that JUP serum concentration is increased in further early stage ovarian cancer subtypes: Endometrioid (1.93 fold-change, p=1.0E-04, n=15), mucinous (1.82 fold-change, p=0.021, n=12) and clear cell carcinoma (1.79 fold-change, p=0.043, n=11) compared to normal control samples (NC, n=39). Difference in sample means was tested using a t-test.

JUP levels in serum from stage I non-serous ovarian subtypes such as endometrioid (n=16; p<0.001), mucinous (n=12; p=0.021) and clear cell carcinomas (n=11; p=0.043) were also significantly elevated when compared to normal controls (n=38) (FIG. 6).

JUP in Other Malignancies

Figure 7:
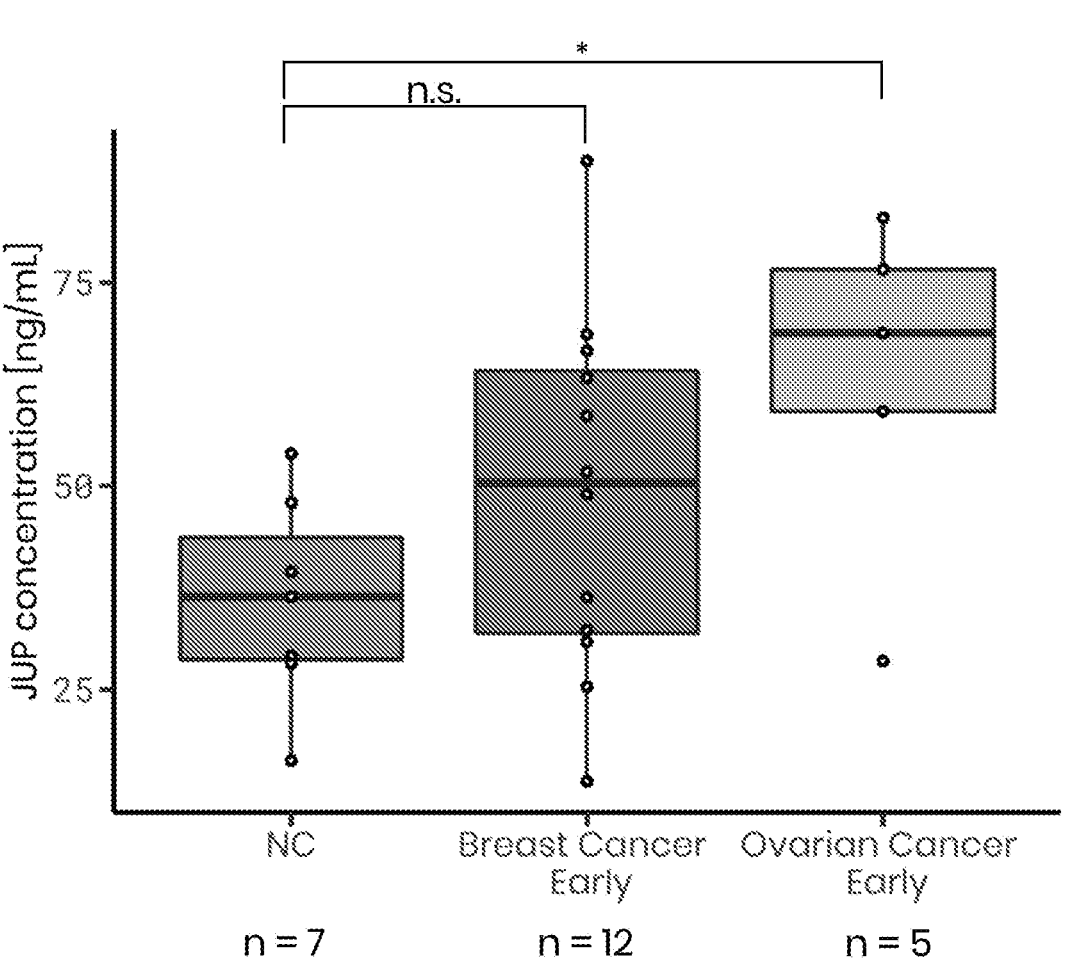
FIG. 7—a plot of ELISA results showing that plasma JUP is not elevated in patients with early stage breast cancer (p=0.122, n=12). P-values were calculated using a t-test.

JUP plasma concentrations were not significantly elevated in early stage breast cancer (n=12, p=0.122) when compared to normal controls (n=7) as measured by ELISA (FIG. 7).

Discussion

This study is the first to employ ovarian vein blood sampling for the identification of biomarkers for early stage ovarian cancer detection. Furthermore, to the best of our knowledge this is also the first report on using saturation labelling 2D DIGE for proteome analysis of depleted serum. The combination of both novel approaches of sampling venous blood from early stage tumors in combination with depletion of the top 14 high abundant proteins and saturation DIGE enabled us to visualize and quantify 2,692 protein spots using 5 μg protein from depleted serum. This greatly increased the number of serum proteins available for quantification as in comparison with traditional LC-MS/MS approaches, which yield identification of around 150 proteins for 1D-LC and approximately 1,000 proteins for 2D-LC approaches using blood samples (Dayon L and Kussmann M, 2013, "A critical comparison of analytical workflows in terms of effort, throughput and outcome", *EuPA Open Proteomics*, 1: 8-16). This renders saturation labelling DIGE a competitive method for proteome analysis of depleted serum. Moreover, the increased level of JUP in patients with early stage ovarian cancer was subsequently validated in samples from an international, multicenter patient cohort, indicating the validity of this approach.

JUP has previously been indicated in other cancers, for example increased expression of JUP in tissue was described in testicular germ cell tumors (Skotheim R I et al., 2002, "New insights into testicular germ cell tumorigenesis from gene expression profiling", *Cancer Research*, 62: 2359-2364), while in prostate cancer a JUP-SOX4 complex was described to modulate Wnt signaling (Lai Y H et al., 2011, "SOX4 interacts with plakoglobin in a Wnt3a-dependent manner in prostate cancer cells", *BMC Cell Biol.*, 12: 50). Further, JUP has been proposed as a tissue biomarker for cervical (neck) lymph node metastasis in tongue squamous cell carcinoma (Kurokawa A et al., 2008, "Diagnostic value of integrin alpha3, beta4, and beta5 gene expression levels for the clinical outcome of tongue squamous cell carcinoma", *Cancer;* 112: 1272-1281), and an increase in protein expression was detected on the cell surface of late stage colorectal cancer samples (Luque-Garcia J L et al., 2010, "Differential protein expression on the cell surface of colorectal cancer cells associated to tumor metastasis", *Proteomics*, 10: 940-952). Moreover, JUP has been implicated as a potential prognostic biomarker for patients with lung adenocarcinoma.

The role and regulation of JUP on a cellular level is complex and has not been fully elucidated. For example, JUP has been shown to modulate p-catenin/Wnt signaling in arrhythmogenic right ventricular cardiomyopathy, where a deletion of JUP activated p-catenin signaling in murine hearts (Li J et al., 2011, "Cardiac tissue-restricted deletion of plakoglobin results in progressive cardiomyopathy and activation of {beta}-catenin signaling", *Mol. Cell. Biol.*, 31: 1134-1144). Further, a deletion of desmoglein-1 resulted in a nuclear localization of JUP and a reduction of Wnt/β-catenin signaling in atrial myocyte cell lines (Garcia-Gras E et al., 2006, "Suppression of canonical Wnt/beta-catenin signaling by nuclear plakoglobin recapitulates phenotype of arrhythmogenic right ventricular cardiomyopathy", *The Journal of Clinical Investigation*, 116: 2012-2021).

JUP is also reported as a potential biomarker for arteriosclerosis (Cooksley-Decasper S et al., 2012, "Antibody phage display assisted identification of junction plakoglobin as a potential biomarker for atherosclerosis", *PloS One*, 7: e47985), however there was no correlation between age and JUP concentration in our early stage ovarian cancer group (p=0.08, FIG. 5). Furthermore, JUP showed no increase in plasma concentrations in early stage breast cancer patients when compared to controls (FIG. 7). This gives evidence for specificity of JUP as a biomarker for early stage ovarian cancer.

A weak correlation of JUP and CA125 concentrations in plasma of Stage 1-3 serous ovarian cancer (ρ=0.39) was found and implies that combining the two measurements could improve detection accuracy of early stage epithelial ovarian cancer (FIG. 5). This was the case in our data set, the combination of JUP and CA125 increased the AUC in Stage1, Stage1A+B and Stage1A patients as in comparison to each individual marker.

Increased CA125 concentration is estimated to be manifested in less than 50% of early stage ovarian cancer patients (Nustad K et al., 1996, "Specificity and affinity of 26 monoclonal antibodies against the CA 125 antigen: first report from the ISOBM TD-1 workshop", International Society for Oncodevelopmental Biology and Medicine. *Tumour biology: the journal of the International Society for Oncodevelopmental Biology and Medicine*, 17: 196-219), while in our samples 81% show a CA125 concentration above 35 kU/L, artificially boosting the AUC of CA125 in early stage patients. The distribution of CA125 concentration in our dataset therefore represents a skewed sampling from the actual distribution of CA125 concentration in blood of all early stage ovarian cancer patients. This limits the usefulness for a combined marker analysis of JUP and CA125 in our dataset.

Combined analysis with a further proposed marker for early stage ovarian cancer, human epididymis protein 4 (HE4) was not undertaken. This is due to the reported moderate correlation of HE4 to CA125 (Partheen K et al., 2011, "Evaluation of ovarian cancer biomarkers HE4 and CA-125 in women presenting with a suspicious cystic ovarian mass", *Journal of Gynecologic Oncology*, 22: 244-252; and Hamed E O et al., 2013, "Significance of HE4 estimation in comparison with CA125 in diagnosis of ovarian cancer and assessment of treatment response", *Diagnostic Pathology*, 8: 11), which was reproduced in our early stage patient dataset as well (ρ=0.72). Therefore, a bias towards higher values of HE4 (as in comparison to normal controls) in the set of early stage patients is expected. This means no additional benefit of a combination of HE4 with JUP was expected in our dataset. It is also of note that HE4 is reported to show no increase in specificity and sensitivity when combined with CA125 (Moore R G, 2009, "A novel multiple marker bioassay utilizing HE4 and CA125 for the prediction of ovarian cancer in patients with a pelvic mass", 112: 40-46; and Moore R G et al., 2008, "The use of multiple novel tumor biomarkers for the detection of ovarian carcinoma in patients with a pelvic mass", *Gynecologic Oncology*, 108: 402-408), likely due to the moderate correlation reported between CA125 and HE4 (Partheen K et al., 2011, supra; and Hamed E O et al., 2013, supra). As mentioned above, a prospective study could account for both CA125 and HE4 bias and would allow for more accurate assessment of the value of the combination of JUP with CA125 and/or HE4 for detection of early stage ovarian cancer.

The data presented in this study consistently shows JUP concentration to be increased in plasma of early stage ovarian cancer patients. It is of note that our results show differences in the detected range of JUP concentration, which renders the data comparable only within the group of the specific ELISA performed with the same lot number and on the same date. Similar issues with reproducibility between ELISA lots were reported before (Ngeh J et al., 2004, "The reproducibility of an enzyme-linked immunosorbent assay for detection of *Chlamydia pneumoniae*-specific antibodies", *Clinical Microbiology and Infection,* 10: 171-174) and show limitation of the method for clinical diagnostics. This means that our measured concentration of JUP should not be used as an accurate absolute quantification, but rather as a relative quantification. A promising alternative to ELISA to address this problem would be the usage of targeted mass spectrometry approaches for absolute quantification (Kito K and Ito T, 2008, "Mass Spectrometry-Based Approaches Toward Absolute Quantitative Proteomics", *Current Genomics,* 9: 263-274; and Rauniyar N, 2015, "Parallel Reaction Monitoring: A Targeted Experiment Performed Using High Resolution and High Mass Accuracy Mass Spectrometry", *International Journal of Molecular Sciences,* 16: 28566-28581).

CONCLUSIONS

The results of this study show that JUP is a biomarker for specific diagnosis of ovarian cancer, including early stage ovarian cancer. This makes it evident that our novel approach of downstream venous tumor blood sampling in combination with saturation labelling DIGE is a viable strategy for cancer biomarker discovery. We expect this combination of techniques to be a valuable tool for additional types of solid tumors in the future.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

It is to be noted that where a range of values is expressed, it will be clearly understood that this range encompasses the upper and lower limits of the range, and all numerical values or sub-ranges in between these limits as if each numerical value and sub-range is explicitly recited. The statement "about X % to Y %" has the same meaning as "about X % to about Y %," unless indicated otherwise.

The term "about" as used in the specification means approximately or nearly and in the context of a numerical value or range set forth herein is meant to encompass variations of +/−10% or less, +/−5% or less, +/−1% or less, or +/−0.1% or less of and from the numerical value or range recited or claimed.

It is also to be noted that, as used herein, the singular forms "a", "an" and "the" include plural aspects unless the context already dictates otherwise.

The subject headings used herein are included only for the ease of reference of the reader and should not be used to limit the subject matter found throughout the disclosure or the claims. The subject headings should not be used in construing the scope of the claims or the claim limitations.

The description provided herein is in relation to several embodiments which may share common characteristics and features. It is to be understood that one or more features of one embodiment may be combinable with one or more features of the other embodiments. In addition, a single feature or combination of features of the embodiments may constitute additional embodiments.

All methods described herein can be performed in any suitable order unless indicated otherwise herein or clearly contradicted by context. The use of any and all examples, or exemplary language (e.g., "such as") provided herein, is intended merely to better illuminate the example embodiments and does not pose a limitation on the scope of the claimed invention unless otherwise claimed. No language in the specification should be construed as indicating any non-claimed element as essential.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

Those skilled in the art will appreciate that the invention described herein is susceptible to variations and modifications other than those specifically described. It is to be understood that the invention includes all such variations and modifications. The invention also includes all of the steps, features, compositions and compounds referred to, or indicated in this specification, individually or collectively, and any and all combinations of any two or more of the steps or features.

Finally, reference is made to standard textbooks of molecular biology that contain methods for carrying out basic techniques encompassed by the present invention. See, for example, Green M R and Sambrook J, 2012, supra.

The invention claimed is:

1. A method of detecting and treating ovarian cancer in a subject or identifying and treating a subject having ovarian cancer, the method comprising:
  (a) detecting an expression level of junction plakoglobin in blood of the subject;
  (b) comparing the expression level of junction plakoglobin in the blood of the subject with a reference expression level for junction plakoglobin, wherein the reference expression level is an expression level for junction plakoglobin in a normal subject or in a subject not having ovarian cancer;
  (c) detecting ovarian cancer in the subject or identifying the subject as a subject having ovarian cancer on the basis of the comparison,
  wherein an expression level of junction plakoglobin in the blood of the subject that is higher than the reference expression level for junction plakoglobin indicates that the subject has ovarian cancer; and
  (d) treating the subject in which ovarian cancer has been detected or which has been identified as having ovarian cancer,
  wherein treating the subject comprises one or more of removal of one or both ovaries of the subject, chemotherapy, and radiotherapy.

2. The method of claim 1, wherein the method is conducted in vitro in a blood sample obtained from the subject.

3. The method of claim 2, wherein the blood sample is a serum sample or plasma sample obtained from peripheral blood of the subject.

4. The method of claim 1, wherein the expression level of junction plakoglobin protein is detected using an antibody specific for the junction plakoglobin protein.

5. The method of claim 1, wherein the ovarian cancer is ovarian epithelial carcinoma, serous ovarian carcinoma, endometrioid ovarian carcinoma, mucinous ovarian carcinoma, or clear cell ovarian carcinoma.

6. The method of claim 1, wherein the ovarian cancer is early stage ovarian cancer, including Stage I ovarian cancer.

7. A method of treating ovarian cancer in a subject, comprising:
  (a) identifying the subject as a subject with ovarian cancer on the basis that an expression level of junction plakoglobin in blood of the subject is higher than a reference expression level for junction plakoglobin, wherein the reference expression level is an expression level for junction plakoglobin in a normal subject or in a subject not having ovarian cancer; and
  (b) treating ovarian cancer in the subject,
  wherein treating ovarian cancer in the subject comprises one or more of removal of one or both ovaries of the subject, chemotherapy, and radiotherapy.

8. The method of claim 7, wherein the expression level of junction plakoglobin has been detected in a blood sample obtained from the subject, including a serum sample or a plasma sample, obtained from peripheral blood of the subject.

9. The method of claim 7, wherein the expression level of junction plakoglobin protein has been detected using an antibody specific for the junction plakoglobin protein.

10. The method of claim 7, wherein the ovarian cancer is ovarian epithelial carcinoma, serous ovarian carcinoma, endometrioid ovarian carcinoma, mucinous ovarian carcinoma, or clear cell ovarian carcinoma.

11. The method of claim 7, wherein the ovarian cancer is early stage ovarian cancer, including Stage I ovarian cancer.

12. A method of treating ovarian cancer in a subject, comprising:
  (a) detecting an expression level of junction plakoglobin in blood of the subject;
  (b) comparing the expression level of junction plakoglobin in the blood of the subject with a reference expression level for junction plakoglobin, wherein the reference expression level is an expression level for junction plakoglobin in a normal subject or in a subject not having ovarian cancer;
  (c) detecting ovarian cancer in the subject on the basis of the comparison, wherein an expression level of junction plakoglobin in the blood of the subject that is higher than the reference expression level for junction plakoglobin is indicative of ovarian cancer in the subject; and (d) treating ovarian cancer in the subject, wherein treating ovarian cancer in the subject comprises one or more of removal of one or both ovaries of the subject, chemotherapy, and radiotherapy.

13. The method of claim 12, wherein the expression level of junction plakoglobin is detected in a blood sample obtained from the subject, including a serum sample or a plasma sample obtained from peripheral blood of the subject.

14. The method of claim 12, wherein the expression level of junction plakoglobin protein is detected using an antibody specific for the junction plakoglobin protein.

15. The method of claim 12, wherein the ovarian cancer is ovarian epithelial carcinoma, serous ovarian carcinoma, endometrioid ovarian carcinoma, mucinous ovarian carcinoma, or clear cell ovarian carcinoma.

16. The method of claim 12, wherein the ovarian cancer is early stage ovarian cancer, including Stage I ovarian cancer.

17. The method of claim 1, wherein the expression level of junction plakoglobin in blood of the subject is at least about 1.7-fold higher than the reference expression level for junction plakoglobin.

18. The method of claim 7, wherein the expression level of junction plakoglobin in blood of the subject is at least about 1.7-fold higher than the reference expression level for junction plakoglobin.

19. The method of claim 12, wherein the expression level of junction plakoglobin in blood of the subject is at least about 1.7-fold higher than the reference expression level for junction plakoglobin.

* * * * *

SEQUENCE LISTING

```
<160> NUMBER OF SEQ ID NOS: 3

<210> SEQ ID NO 1
<211> LENGTH: 3586
<212> TYPE: DNA
<213> ORGANISM: Homo sapiens

<400> SEQUENCE: 1
gaggtggcga ggggcgtggc ttggctgtca ggtctcttcg ccttttgttc ggttactgag       60
ttgctgcctt ggccagagtc cggagcagcc gccgcccgac cacgccgagc tcagttcgct      120
gtccgcgccg gctcccaccc cggcccgacc ccgacccggc ccggtcaggc cccatactca      180
```

-continued

```
ggtgcgggct atcggggggcg cagtagccac gatggaggtg atgaacctga tggagcagcc      240
tatcaaggtg actgagtggc agcagacata caccctacgac tcgggtatcc actcgggcgc     300
caacacctgc gtgccctccg tcagcagcaa gggcatcatg gaggaggatg aggcctgcgg      360
gcgccagtac acgctcaaga aaaccaccac ttacacccag ggggtgcccc ccagccaagg      420
tgatctggag taccagatgt ccacaacagc cagggccaaa cgggtgcggg aggccatgtg      480
ccctggtgtg tcaggcgagg acagctcgct tctgctggcc acccaggtgg aggggcaggc      540
caccaacctg cagcgactgg ccgagccgtc ccagctgctc aagtcggcca ttgtgcatct      600
catcaactac caggacgatg ccgagctggc cactcgcgcc ctgcccgagc tcaccaaact      660
gctcaacgac gaggacccgg tggtggtgac caaggcggcc atgattgtga accagctgtc      720
gaagaaggag gcgtcgcggc gggccctgat gggctcgccc cagctggtgg ccgctgtcgt      780
gcgtaccatg cagaatacca gcgacctgga cacagcccgc tgcaccacca gcatcctgca      840
caacctctcc caccaccggg aggggctgct cgccatcttc aagtcgggtg gcatccctgc      900
tctggtccgc atgctcagct cccctgtgga gtcggtcctg ttctatgcca tcaccacgct      960
gcacaacctg ctcctgtacc aggagggcgc caagatggcc gtgcgcctgg ccgacgggct     1020
gcaaaagatg gtgcccctgc tcaacaagaa caaccccaag ttcctggcca tcaccaccga     1080
ctgcctgcag ctcctggcct acggcaacca ggagagcaag ctgatcatcc tggccaatgg     1140 tgggcccccag gccctcgtgc agatcatgcg taactacagt tatgaaaagc tgctctggac     1200
caccagtcgt gtgctcaagg tgctatccgt gtgtcccagc aataagcctg ccattgtgga     1260
ggctggtggg atgcaggccc tgggcaagca cctgaccagc aacagccccc gcctggtgca     1320
gaactgcctg tggaccctgc gcaacctctc agatgtggcc accaagcagg agggcctgga     1380
gagtgtgctg aagattctgg tgaatcagct gagtgtggat gacgtcaacg tcctcacctg     1440
tgccacgggc acactctcca acctgacatg caacaacagc aagaacaaga cgctggtgac     1500
acagaacagc ggtgtggagg ctctcatcca tgccatcctg cgtgctggtg acaaggacga     1560
catcacggag cctgccgtct gcgctctgcg ccacctcact agccgccacc ctgaggccga     1620
gatggcccag aactctgtgc gtctcaacta tggcatccca gccatcgtga agctgctcaa     1680
ccagcccaac cagtggccac tggtcaaggc aaccatcggc ttgatcagga atctggccct     1740
gtgcccagcc aaccatgccc cgctgcagga ggcagcggtc atcccccgcc tcgtccaact     1800
gctggtgaag gcccaccagg atgcccagcg ccacgtagct gcaggcacac agcagcccta     1860
cacggatggt gtgaggatgg aggagattgt ggagggctgc accggagcac tgcacatcct     1920
cgcccgggac cccatgaacc gcatggagat cttccggctc aacaccattc ccctgtttgt     1980
gcagctcctg tactcgtcgg tggagaacat ccagcgcgtg gctgccgggg tgctgtgtga     2040
gctggcccag gacaaggagg cggccgacgc cattgatgca gaggggggcct cggccccact     2100 catggagttg ctgcactccc gcaacgaggg cactgccacc tacgctgctg ccgtcctgtt     2160
ccgcatctcc gaggacaaga acccagacta ccggaagcgc gtgtccgtgg agctcaccaa     2220
ctccctcttc aagcatgacc cggctgcctg ggaggctgcc cagagcatga ttcccatcaa     2280
tgagccctat ggagatgaca tggatgccac ctaccgcccc atgtactcca gcgatgtgcc     2340
ccttgacccg ctggagatgc acatggacat ggatggagac taccccatcg acacctacag     2400
cgacggcctc aggcccccgt accccactgc agaccacatg ctggcctagg cggcctggcc     2460
ccagtacggc ccccctcttg caggcttttc ctcctctcta gaacctcctt ctgttggagg     2520
ccctcccatc tccccgctga aacctgcgct cctttttttgg ggggatcctt tgctgctgag     2580
```

-continued

```
cttccccaag cacggtgtgc cctggcctgc cttcttcttg tgtctttggt ggggatgggg      2640
aggcctattc ctgctggccc cttctggggg tggtgggcag gtgacacgga gtggcttgag      2700
cttctgggga tgcaggtcca ccgagcccct gacccctgtc tgtccccgct ccctaacag      2760 gtgcggttcc tcatctgaga ggctctccgt gcaggcgatg gggcaagaca gaaaagtgcc      2820
tgagctgggg aagccggggt gtaacttcct gctgcaccct gcgcctccag aggtcctccg      2880
tagggtcttt cttgggatag tgttctgctc ctgcttttct gtcctgggca tgggtccagg      2940
gcctgacacc ccctcccgc ccctgtggcc ctggccacta aagcttcaga ctcaagtacc      3000
cattctgttt tcccccagca acgcccctcc aaacctccag cctccctgtc tccagctgcc      3060
tgggcccgga agggctttgg ttccttctct gggtctgatt ttctcactga actccaccga      3120
ccaactgccc taagccccca gggcctccag ggcccaggtt cgagacccaa accccccaaa      3180
tccaaaactt ctcttgaaaa gttcagggac cgtccagggg agatggggag gagatatgga      3240
gtgagtcacc tgctccagaa gatgccagct tctctctcca gggtgcttag ttggctttgc      3300
ccacccctca ctccccaggg agctctgggg acagcttcct cacacccctg tcccacccac      3360
acagctgccc tagctgaccc cgagaagtgc tcttggctga cccctctggt gtgtggtgag      3420
gggctttctc ttccccttcc tgtttcagac ccccccattt cccgcacatg gtgtgggggg      3480 ctggggagg tccaagcaga gtgtttatt attatcgctt tatgtttttg gttattggtt      3540
tttttgtata gaccaaagca aagaaaataa aaataacaca gatgcg                     3586
```

```
<210> SEQ ID NO 2
<211> LENGTH: 745
<212> TYPE: PRT
<213> ORGANISM: Homo sapiens

<400> SEQUENCE: 2

Met Glu Val Met Asn Leu Met Glu Gln Pro Ile Lys Val Thr Glu Trp
1               5                   10                  15

Gln Gln Thr Tyr Thr Tyr Asp Ser Gly Ile His Ser Gly Ala Asn Thr
            20                  25                  30

Cys Val Pro Ser Val Ser Ser Lys Gly Ile Met Glu Glu Asp Glu Ala
        35                  40                  45

Cys Gly Arg Gln Tyr Thr Leu Lys Lys Thr Thr Thr Tyr Thr Gln Gly
    50                  55                  60

Val Pro Pro Ser Gln Gly Asp Leu Glu Tyr Gln Met Ser Thr Thr Ala
65                  70                  75                  80

Arg Ala Lys Arg Val Arg Glu Ala Met Cys Pro Gly Val Ser Gly Glu
                85                  90                  95

Asp Ser Ser Leu Leu Leu Ala Thr Gln Val Glu Gly Gln Ala Thr Asn
            100                 105                 110

Leu Gln Arg Leu Ala Glu Pro Ser Gln Leu Leu Lys Ser Ala Ile Val
        115                 120                 125

His Leu Ile Asn Tyr Gln Asp Asp Ala Glu Leu Ala Thr Arg Ala Leu
    130                 135                 140

Pro Glu Leu Thr Lys Leu Leu Asn Asp Glu Asp Pro Val Val Val Thr
145                 150                 155                 160

Lys Ala Ala Met Ile Val Asn Gln Leu Ser Lys Lys Glu Ala Ser Arg
                165                 170                 175

Arg Ala Leu Met Gly Ser Pro Gln Leu Val Ala Ala Val Val Arg Thr
            180                 185                 190
```

-continued

```
Met Gln Asn Thr Ser Asp Leu Asp Thr Ala Arg Cys Thr Thr Ser Ile
        195                 200                 205

Leu His Asn Leu Ser His His Arg Glu Gly Leu Leu Ala Ile Phe Lys
        210                 215                 220

Ser Gly Gly Ile Pro Ala Leu Val Arg Met Leu Ser Ser Pro Val Glu
225                 230                 235                 240

Ser Val Leu Phe Tyr Ala Ile Thr Thr Leu His Asn Leu Leu Leu Tyr
                245                 250                 255

Gln Glu Gly Ala Lys Met Ala Val Arg Leu Ala Asp Gly Leu Gln Lys
                260                 265                 270

Met Val Pro Leu Leu Asn Lys Asn Asn Pro Lys Phe Leu Ala Ile Thr
        275                 280                 285

Thr Asp Cys Leu Gln Leu Leu Ala Tyr Gly Asn Gln Glu Ser Lys Leu
        290                 295                 300

Ile Ile Leu Ala Asn Gly Gly Pro Gln Ala Leu Val Gln Ile Met Arg
305                 310                 315                 320

Asn Tyr Ser Tyr Glu Lys Leu Leu Trp Thr Thr Ser Arg Val Leu Lys
                325                 330                 335

Val Leu Ser Val Cys Pro Ser Asn Lys Pro Ala Ile Val Glu Ala Gly
                340                 345                 350

Gly Met Gln Ala Leu Gly Lys His Leu Thr Ser Asn Ser Pro Arg Leu
        355                 360                 365

Val Gln Asn Cys Leu Trp Thr Leu Arg Asn Leu Ser Asp Val Ala Thr
        370                 375                 380

Lys Gln Glu Gly Leu Glu Ser Val Leu Lys Ile Leu Val Asn Gln Leu
385                 390                 395                 400

Ser Val Asp Asp Val Asn Val Leu Thr Cys Ala Thr Gly Thr Leu Ser
                405                 410                 415

Asn Leu Thr Cys Asn Asn Ser Lys Asn Lys Thr Leu Val Thr Gln Asn
        420                 425                 430

Ser Gly Val Glu Ala Leu Ile His Ala Ile Leu Arg Ala Gly Asp Lys
        435                 440                 445

Asp Asp Ile Thr Glu Pro Ala Val Cys Ala Leu Arg His Leu Thr Ser
        450                 455                 460

Arg His Pro Glu Ala Glu Met Ala Gln Asn Ser Val Arg Leu Asn Tyr
465                 470                 475                 480

Gly Ile Pro Ala Ile Val Lys Leu Leu Asn Gln Pro Asn Gln Trp Pro
                485                 490                 495

Leu Val Lys Ala Thr Ile Gly Leu Ile Arg Asn Leu Ala Leu Cys Pro
                500                 505                 510

Ala Asn His Ala Pro Leu Gln Glu Ala Ala Val Ile Pro Arg Leu Val
        515                 520                 525

Gln Leu Leu Val Lys Ala His Gln Asp Ala Gln Arg His Val Ala Ala
        530                 535                 540

Gly Thr Gln Gln Pro Tyr Thr Asp Gly Val Arg Met Glu Glu Ile Val
545                 550                 555                 560

Glu Gly Cys Thr Gly Ala Leu His Ile Leu Ala Arg Asp Pro Met Asn
                565                 570                 575

Arg Met Glu Ile Phe Arg Leu Asn Thr Ile Pro Leu Phe Val Gln Leu
        580                 585                 590

Leu Tyr Ser Ser Val Glu Asn Ile Gln Arg Val Ala Ala Gly Val Leu
        595                 600                 605

Cys Glu Leu Ala Gln Asp Lys Glu Ala Ala Asp Ala Ile Asp Ala Glu
```

-continued

```
            610             615             620
Gly Ala Ser Ala Pro Leu Met Glu Leu Leu His Ser Arg Asn Glu Gly
625                 630             635                 640

Thr Ala Thr Tyr Ala Ala Ala Val Leu Phe Arg Ile Ser Glu Asp Lys
                645             650             655

Asn Pro Asp Tyr Arg Lys Arg Val Ser Val Glu Leu Thr Asn Ser Leu
            660             665             670

Phe Lys His Asp Pro Ala Ala Trp Glu Ala Ala Gln Ser Met Ile Pro
        675             680             685

Ile Asn Glu Pro Tyr Gly Asp Asp Met Asp Ala Thr Tyr Arg Pro Met
        690             695             700

Tyr Ser Ser Asp Val Pro Leu Asp Pro Leu Glu Met His Met Asp Met
705             710             715             720

Asp Gly Asp Tyr Pro Ile Asp Thr Tyr Ser Asp Gly Leu Arg Pro Pro
                725             730             735

Tyr Pro Thr Ala Asp His Met Leu Ala
            740             745
```

```
<210> SEQ ID NO 3
<211> LENGTH: 16306
<212> TYPE: DNA
<213> ORGANISM: Homo sapiens
<220> FEATURE:
<221> NAME/KEY: misc_feature
<222> LOCATION: (10569)..(10668)
<223> OTHER INFORMATION: n is a, c, g, or t

<400> SEQUENCE: 3
ttaaaaaaaa acataccgtt aatttaaatt tctaaccttt agcagtttct gagtgctttc      60
acaaacctga cctcatttaa tccccacata ctccagtgag gtagatatgg ctaatgtatc     120
cagtttacag aagaggagaa acagggtgaa gtaacttgcc taaaatcata ccaagtggga     180
gaagaccaaa cctggccttc taattctaaa tcccaggagt actccatctt tcgggaaaaa     240
aatcccaccc cagcacaaag cctatgaaat gctatacaaa tatgtgatta ctactttggg     300
gcaaggatga ataagcccaa agaagcatca tgcctgacgc tgagttggct ggccggtgaa     360
ggcgtctgtc ccttcccttg gtatccctat gacttacctg ttggacaggt agggggaagg     420
ggagagtaat gagtctcacc tgctcagagc aagggtgggg caagacacac cccatccctt     480
ccattggttt tttccttagt cttactgaca gagccttgtc caatcaggag gaagtaactt     540
tctatctgcc aatagatgca atgttaggat gagacctcaa gttagagtcc atccctagag     600
ccgactggca gtccccgggg ccaatggcaa gcggataaac agaggcggcc gtggaagagg     660
actggaggcg aggctccgcc cctccacggg acagtcaggc gagatagcca gtgagctcgc     720
accagagggt gggcgtctcc cccaggggcg gagcttcgag gtggcgaggg gcgtggcttg     780
gctgtcaggt ctcttcgcct tttgttcggt tactgagttg ctgccttggc cagagtccgg     840
agcagccgcc gcccgaccgc gccgagctca gttcgctgtc cgcgccggct cccaccccgg     900
cccgaccccg acccggcccg gtcaggcccc atactcagta gccacgatgg aggtgatgaa     960
cctgatggag cagcctatca aggtgactga gtggcagcag acatacacct acgactcggg    1020
tatccactcg ggcgccaaca cctgcgtgcc ctccgtcagc agcaagggca tcatggagga    1080
ggatgaggcc tgcgggcgcc agtacacgct caagaaaacc accacttaca cccagggggt    1140
gccccccagc caaggtcagg acccctgggg actattgcat ggggcagaaa acctgcctgg    1200
gtcctggaga gaggtcagag tgaaaggagg cagattgtag ggggtctctg gtctgaggga    1260
```

```
ggaggcacag ctcatgctaa ctaggggccc acccagtctg aaggaggagg tgcagctact    1320
tcagggtgct gcatctggga gggtcacaga atcctcttct gtgaaccatc agtagggagg    1380
gaaggcatag tccctgccct tagggtgcct ccagtctgaa ggaaaagcca tagtccttgc    1440
cttctgtgaa cataagaatc tgatgaagac attgggtacg gtggctcatg cctgtaatcc    1500
cagcactttg ggaggctgag gtgggcagat cacctgaggt caggagtttg agaccagcct    1560
ggccaacatg atgaaacccc gtctctacta aaaatacaaa aattagccgg gtgtggtggc    1620
gcatgcacct gtagtcccag ctacttggga ggctgaggca ggagaattgc ttgaacccag    1680
gaggcagagg ttggagtgag ctgagattgc gccactgcac tccagcctgg gcgacagagt    1740
gagactccgt ctcaaaaaat agtaaaaaaa agagtctgat gaggatgtat actatggctc    1800
tcagggagcc catggatggc agggaggacg cagccctttg gctgcaggag cctcacgttt    1860
gtgggagagc cagggccgta gcccccagga acccccaggg attccccttt gggtagaggg    1920
gtgtaggtgt caagcctgag ggcccctcgt tggggttgga gggagaccag gcctctgcgg    1980
ctgacctgca gataggccaa ggctgtggga tgagtgactg actcagctct ggggcttagt    2040
ccgggatggg gatgcccgc cagcccaagc ctcccctgcc cctctgggag agaggaatag    2100
ccaggcccta gaactgttgg ccacaggtgc ctccagggcc ctgaacatgc caggggggtgg    2160 gctgtgggtg ctgggagtag tgtgagtaga ctgtggctgg tggggctcta tggagctcag    2220
ccctcgcatg ccagtctcct ccctgacagc tggtaggggt agcagggggc cttttggctg    2280
gcagggccag gcactgtgtt ggtagcaaaa agtacagcat ccaggtggga aagccatgca    2340
gctgtctcct ccttctcgac taattagagg gtggaacctc tgcgtccctc tccctggggg    2400
catcaggaca gttgccaggg tgtggctgct tgggcaccta cctgtgggac tcccagaccc    2460
acccagggga tggaagctag agaggaacct gacgtctcag ctgaggaccc agctcctgct    2520
ctctgaaccc acagccctga ctttccctct gatctgctgt gagatgtgat gttggtggtt    2580
ctctgggcct ctgtttgcct gcctgtatag tgggaggatt gctaccgttg gggatgatga    2640
gggtgtaatt agactcctga gatttcaggg ttgaaaacag acctgatggg taagggagga    2700
gaatagagta ggggtttggg cccctgagtc aggctgcctt ataacccctc tgtgcccagt    2760
tttcccatct gtaaagtgga gccagtgata gtacttacct tgcagggtcg ttgtcaggtt    2820
atgtgagaaa atataagcag ggcattgaat tcactgccag gcacataata agtgtgccaa    2880
aaaaaaaaaa aaaattcccg tgatagacag aacatgtggg gcctatttta cagagattac    2940
tgaggtgatg gtgacttccc caaggttcct ggtgagaggg agaatggcca gtcatgtgct    3000 ggggggtttgg gcagggcaag aggtagccca gaggacccag gtggggctgt ctgtggcctg    3060
ccctgctccc cagtgtctgc ccagcccact gcctgcactc agtccctgtc cccatggccc    3120
ccaggtgacc tggagtacca gatgtccaca acagccaggg ccaaacgggt gcgggaggcc    3180
atgtgccctg gtgtgtcagg cgaggacagc tcgcttctgc tggccaccca ggtggagggg    3240
caggccacca acctgcagcg actggccgag ccgtcccagc tgctcaagtc ggccattgtg    3300
catctcatca actaccagga cgatgccgag ctggccactc gcgccctgcc cgagctcacc    3360
aaactgctca cgacgagga cccggtctgt gagggtccct gctagggtgg gggctgggca    3420
gggaggggag agagcagatg tcctcagggg agggacattg tagggggtgga gggaggttat    3480 gacccagact ctcccgtgtg tgatgagtct gactggggcc ctcctcagct ctgtggaagg    3540
gtatcccggc ctctccttag tgctcacgtc cccgcccctg cctttgccct ccaggtggtg    3600
```

-continued

```
gtgaccaagg cggccatgat tgtgaaccag ctgtcgaaga aggaggcgtc gcggcgggcc   3660
ctgatgggct cgccccagct ggtggccgct gtcgtgcgta ccatgcagaa taccagcgac   3720
ctggacacag cccgctgcac caccagcatc ctgcacaacc tctcccacca ccgggagggg   3780
ctgctcgcca tcttcaagtc gggtggcatc cctgctctgg tccgcatgct caggtaccca   3840
ccctgctcac tgcatgagcc caggaccccc tctcacttgg gcctctcccc tcccttccct   3900
gagcttccat aaatatccag tgagcaccta ctatgtgcca ggcagaagca caccccatcc   3960
gggtgctcgg tggctcacag cccagcaggg aacacaggca tgtaaacagc aggttaatga   4020
tcaggatacg acacaggcta tggcagaaga gcattgagat tgctcaaagg tggaatcgct   4080
taatggcagg ggattgacag atgagtggag tttggctagt gtagaggaag ggaagagtgt   4140
cccaggcaga gggaacagca aatgcaaagt cccttgcaaa ctttctgttt cctggccccc   4200
tacaaaatgt ggattggcct catttctttt ttttttttg agatgaggcc ttgctctgtc   4260
acccaagctg gagtgcagtg gcgtgatctc agctcactgc agcctccacc tcctgggttc   4320
gaatgattct cctgcctcag tctcctgagt agctgggatt acaagcatct gccaccatac   4380
ctagctattt tttttttgt tttgagatgg agttttcctc ctgttgccca ggctggagtg   4440
caatggcaca gtctcggctt actgcaacct ctgcctcccg ggttcaagag attctcctgc   4500
ctcagcctcc caagtagcag ggattacagg cacccacgac catgcctggc taattttttgt   4560 attttagta aaaatggggt ttcaccatgt tggccaggct agtcttgaac tcctgacctc   4620
aggtgatctg cccccctggg cctcccaaag tgctgggatt ataggcgtct gccaccatgc   4680
ccagctcaat tttgtatttt tagtagagac ggggtttcac cacgttggcc aggctggttt   4740
cgaactccta acctcagggt gatccacctg cctcagcctc cccaagcgct gagtttacag   4800
acgtgagcca ctgctcctgg ccttatttct catccccata ccaggctgga agctccctga   4860
aggggagact gatttcactc ccctctgaac gccttgcaag gcctctctaa tatgtggcct   4920
tccacatggt ggttacttag tagggatcag tgtctagggg acctactgtg cgctcagcac   4980
agggctgggg actcagaagc aggaggagtc attgtcccag ttgggagaag agaggtgctg   5040
tttgcttcat gcttaagagc agggcaggct caaggagtga tgagatttta gcgaagggat   5100
atttccagag gggcgtcagt agcggggagg cttcctgggg gaggtgggaa cccatgccag   5160
gctcacatgt atgccaggcc tctgggacct cagcgtacta acccctgccc accccccag   5220 ctccctgtg gagtcggtcc tgttctatgc catcaccacg ctgcacaacc tgctcctgta   5280
ccaggagggc gccaagatgg ccgtgcgcct ggccgacggg ctgcaaaaga tggtgcccct   5340
gctcaacaag aacaacccca agttcctggc catcaccacc gactgcctgc agctcctggc   5400
ctacggcaac caggagagca aggtgggccc tccccaaccc tcccgaggcc tgaagcccac   5460
ccttgcgcca tcttctatcc tgcacagcct tgggccgctg cccccttact cctttttagat   5520 gagatatagg tgcagatata catgcttcat catgcgactg aattgcccag aattattatt   5580
ttgaggataa gggaaaaaaa aaatcactca tcctcatata gccactattg tcattcgatg   5640
tgcttcctta agagctgttc tgtgggcaga ttacagatgt gtacacatcc ttgtcatcat   5700
aacaatctgc aatattgcat ctgtttctgc ctgatttttt ttttttttt ttgaaacagg   5760 gtctaacttt gtcacacagg ctagagtgca gtggtgtaat cagggctcac tgcagccttg   5820
acttcctggg ctcagatgat cctcctacct cagcctccag agtagctggg acttcaggcg   5880
tgtgctacca cgcccgacta attttttttt tccttttctt ttctttcttt ttttttttg   5940 tttgagatgg agtctcactt tgtcacccag gcaggagtgc aatggcacga tctcggctca   6000
```

```
ctgcaacctt cgcctcccgg gttcaagcga ttctcctgct tcagcctccc aagtagctag    6060
gattacaggt gcccgccacc acacccagct aattttgta tttttagtag agacaaggtt    6120
tcaccacatt ggccaggctg gtctcgaact cctgacctta ggttgtccat ctgcctcggc    6180
ctaataaaat gctgggatta caggcatgag acaccgtgcc ccacccccaa ctaatttttt    6240
atagagatgg gatttctcca tgttgcccag gctggtctca aactcctggg ctcaagtgat    6300
ctgcctgcct tggcctccca aagtatcagg attacaggtg tgagccactg tgcctggcct    6360
gtatgatgtt taaaaaaaat tttttttgc tatattgtcc tcaaaaccac cctctaataa    6420
tgacagattg cctttccttt cccttttccc cctccccttt cctttttcct tttccttttc    6480
cttttccttt ccctctcttc ctctctttct tctttccttc ccattctttc cttttctttc    6540
ttttttgaga cagggtctca ctgtgttacc caggctagag tgcagtggca tgatcctagc    6600
tcactgcatc ctcaaactcc tgagctcaag cattcgtccc atcttagtct tcctgatagc    6660
taggactatg agaacatact actgagctaa ttagcacccg ggctaagttt taaatttttt    6720
gtggggatgg tgtcttgctc tgttgcccag gctaccctca aggaatcctc ctgcttcagc    6780
ctccgaaatg ctgggattaa agtcatgggc caccataccc agcctacaga tagcatttca    6840
ttaagtggag acctcaggct ttattctgag ggagggtatt tagattgctc ctattccacc    6900
tttataaaca atgctgtaat gaatgtctag cctttgtcaa agagcggaaa aaattctcat    6960 caattttaa cacttctagg cttttcccca aatggccaga ttgatttcca gaaggattgg    7020
actaatttcc agtgccataa ctggtaatgg gtgtgcatat agttttgtca tgtccttgtc    7080
agcactgggt attatccttt tttcaaaatt ttggcttaca taacagtcat gaaactattg    7140
gggtgggctg ggtgtggtgg ttcacgcctg taatcccagc actttgggag gcagaggcgg    7200
gtgaattgcc tgaggtcagg agtttgaaac cagcctggcc aacatagtga aaccctgtct    7260
ctaccaaaaa ctacagaaat tagccgggcg tgatggcaca cgcctgtaat cccagctact    7320
tgggaggctg aggcatgaga attgcttgaa cccgggaggc ggaggttgta gtgacctgag    7380
atcgtgccac tgcactccag cctgggtgac agagcgagac tctatctcaa aaaaaaaaac    7440
aaaaaaactt attggggtgc ttggctgggt gtggtggctc acatctgtaa tcccagcact    7500 ttggaggct gaggtgtgag gatcacttga ggccaggagt tctagaccag cctgggcagc    7560
atagtgagac ccccatcttt ataaaaagaa aaaatacat aaaagaaaa aaacgaacta    7620 ttcgtgcttt agctgaagct cagtaatgac agttctgtct cctgtcccgc gcttccttgt    7680
tcctgtcata ttccccgtcc atctcacact cattccctct ttacccatag ctgatcatcc    7740
tggccaatgg tgggccccag gccctcgtgc agatcatgcg taactacagt tatgaaaagc    7800
tgctctggac caccagtcgt gtgctcaagg tgctatccgt gtgtcccagc aataagcctg    7860
ccattgtgga ggctggtgag tatgatggcc ttgagggcgg ctggggtggg agctctgccc    7920
agctgccagg ctcagtcagc catgctcccc gtggctgatg gcaccccat ccctgcccca    7980 ggtgggatgc aggccctggg caagcacctg accagcaaca gccccgcct ggtgcagaac    8040 tgcctgtgga ccctgcgcaa cctctcagat gtggccacca gcaggtgag ggaggtatct    8100 gggcctgggg ttgacctctt cagctgcccc atccagcctc ctgtctgggc atctgacctg    8160
aggtactgtg ggaggactgg gggctctaaa tctctcttcc ttgtgactga ggctggaaat    8220
gccttgaaaa ccctcatctc ttttttttttt tttttttttt tttttcctga cggagtctca    8280
ctctgtcacc taggctggag tgcagtggtg caatctcggc tcactgcaag ctccgcctcc    8340
```

```
tgggctcaag tgattctcct gcctcagcct cccgagtagt tgggactaca ggcacctgcc     8400
atcatgtctg gctaattttt gtattttat ggagacaggg tttcaccatg ttgggcaggc      8460
tggtcttgaa ctcctgacct caggtgatcc acccgccttg gcctcccaaa gtgctgggat     8520
tacaggcgtg agccaccaca tccagcaaaa gaacagtttt gacctgggcc ctgggctgga     8580
gcaatagtgt accaagagac aggcccccat gactaaaaat acaatttaag gaaaaatgca     8640
gctccagggc aagtgccctg tgcctccttc caacaaccat tccccaggcc tcccctagca     8700
atatgctgtt tatcaagtgc tcaccctgtg ctggccctct gcgtggcatt tgtggacagt     8760
agctcattca acctgggggtt agagtgtggg accccgtggg ttagatgaag acactgaggc     8820
tcggggagct aatggccatg gtcacaggta gtaaatggca gaactgggat ttgaacccag     8880
gactgtccgt ccccaaagct ggggtttttc tgttccacca caaggcccac gtgtctccct     8940
gggagaagtg agatagacgt ctgaggtagt gattttactg gaaatggatt tggctcaggg     9000
ccccagggtg gtggggcagc agtgaaggcc cagaaaggtg acaagcgagt agacatggct     9060
cagctgggcc actgaatcat gcggccccct caacaattgc ctcctggtct cgaggcctcc     9120
cttggccacc gtactttggc ctgaggaggg ttctgcctgg gtctgagggc cccagggaaa     9180
ggctgatgag ttggagggaa gagatgtggg gcttagagcc aagcctgggt tcagatccag     9240
ccactagctg tgtgtctgtg ggcaagttcc ccaacctctc tgagcctcat tgcctcactt     9300
gcaccacagg atagtaacgc cctctcacag ggtgtggcgg gtcataggga tgaaagttcc     9360
cgggcacaca caggcagggc tgaccccttt aggtcatccc actcccccttg gacatattcg     9420 agaaggctcc ctggagttgg ctgctccctg actcccccgt cccttccttg ccctccagga     9480
gggcctggag agtgtgctga agattctggt gaatcagctg agtgtggatg acgtcaacgt     9540
cctcacctgt gccacgggca cactctccaa cctgacatgc aacaacagca agaacaagac     9600
gctggtgaca cagaacagcg gtgtggaggc tctcatccat gccatcctgc gtgctggtga     9660
caaggacgac atcacggagc ctgccgtctg cgctctgcgc cacctcacta gccgccaccc     9720
tgaggccgag atggcccaga actctgtgcg tctcaactat ggcatcccag ccatcgtgaa     9780
gctgctcaac cagcccaacc agtggccact ggtcaaggta ctgctgttag gcgaggggag     9840
gagctccctg cagcaggctt aggtgctgta ttggtatagg caaagccgct gtagcaaaga     9900
agccctaaat acagtggctc gaataagaca gaagtttatt tctctctcgt gtaatagttt     9960
agacctcaac aatggctctg ctctaaaatt ccagaattgg gatttctatc ttgtagctct     10020
accagcccct agggcagagc tcagagttca aaatgcacat gagtaccctg ggtggtttca    10080
ttaaattgca ggttccaggg ccaggcacgg tggctcatgc ctgtaatccc aacactttgg    10140
gaggcaaagg taggaggatt gcttgaggcc aggaatttga gaccagtctg gacaacatag    10200
caagacctgt ctcgacaaca ataacaacaa cagaaattag ccaggtgtgg tggtgcacgc    10260
ctgtggtccc agctactggg gaggggaggc tcaggttgga ggatcgcttg agcacaggag    10320
ttggaggtta cagtgagcta tgattgcatc agtgcactcc agcctgggtg acagagcaag    10380
aacccgtgtc ttaaaagaaa agaaaaacag gaggctgggt gcagtggctc acatctgtag    10440
ttccagcact ttgggaggtg caggcagagg cggaagcgga aggatcactt gaggccagga    10500
gtttgagacc atcatgggta acatagtgag acacccatct cttacaaaaa atttggaaaa    10560
aaaaaaaann nnnnnnnnnn nnnnnnnnnn nnnnnnnnnn nnnnnnnnnn nnnnnnnnnn     10620
nnnnnnnnnn nnnnnnnnnn nnnnnnnnnn nnnnnnnnnn nnnnnnnnct cacgcctgta     10680
atcccagcac tttggaagga cggggcggga ggattacctg aagttaggag ttcgagacca    10740
```

-continued

```
gcctggccaa catagtaagt ccccgcctcc acaaaaaata caaaaattag ctggccatgg  10800
tggcatgtgc ctgtaatctc agctactcgg aaggctgagg cagaagaatt acttgaaccc  10860
ggaaggcaga ggttgcagtg agctagatcg ctcattgcac tccagcctgg gtgacagaga  10920
gagactccgt cttggaaaac aaaaacaaaa aacatggcca ggcgtgagcc actgcgcccg  10980
gcctatacat tgaattaaaa aaagaaaatt catgtttaga aaaaaaaatg tcattgtgac  11040
ccctccttga tgcttggtcc ctgctgcaaa cctgaggtgg gactttgcat cctacccagc  11100
agctaagtgg caagtgactt tggcaagtca tttgccctgt gctcacgtcc ccatctcaca  11160
tgattttcat ccctgtcctc ctggcgtctt gttttgagga tgaaatagat gacaccttga  11220
gaggctctgg gaggccagag tggctcctct gagtcaaaga ccctggggag gagatctcag  11280
gacacctctt tccagagctg ccctgctggg gattaatgac aatgtgagca ccacccaagc  11340
aggaggcttc gggggcacct agagcacaga attcctgaga atcaggcttg gaggactatc  11400
acaaaagcaa gcaaggtcat ggtgtctgtg ggggtggtt aagaaagagg ggacagggtg  11460
aggggccagg catgggctg gcaggatgtt ctggaatggg gtgtcatttt agcaagggct  11520
attagaatta gccatgagca gccggacgtg gtagcccaca cctgtaatcc cagcacttta  11580
gaaggcagaa gcaggcggat cacctgaggt caggagttcg aggccagcct gcccaacatg  11640
gcgaaaccct gtctctacta aaaatacaaa aaattagctg ggcatggtgg caggcacctg  11700
taatcgcagc tactcaggag gctgaggcag gagaatcgct tgaacccagg aggtggaggt  11760
tgcagtgagg tgagattgca ccactgcact ccagcctggg tgacaagagc gaaactctgt  11820
ctcaaaaaaa aaaaaaaaaa agaattagcc atgagcactc ccagatcctg tggattaagt  11880
gacatggctg ggatggtctc cttctctgga tattttccag tatgtctgtg tctggcctcg  11940
gggacagaag aggtgaagga gggaagggat acttgaagct gggaagctgg gatccttcag  12000
atgtccaaga agtgccccctg atcactgccc ctttttttgc caggcaacca tcggcttgat  12060
caggaatctg gccctgtgcc cagccaacca tgccccgctg caggaggcag cggtcatccc  12120
ccgcctcgtc caactgctgg tgaaggccca ccaggatgcc cagcgccacg tagctgcagg  12180
cacacagcag ccctacacgg tatgtgagct ggtggtgcct ctgacagcct tcctggggggg  12240 tcagggtgtc ctctgtgggt gtgtgtgtga atgggggaggt cagttgcaac tgatgccaat  12300
tccaagaacc tgtgaagttc attcggctgt catggggagg agttgtggcc atgtccaagg  12360
cacctgtccc atgcccccctg cctcctctca cacaggatgg tgtgaggatg gaggagattg  12420
tggagggctg caccggagca ctgcacatcc tcgcccggga ccccatgaac cgcatggaga  12480
tcttccggct caacaccatt cccctgtttg tgcaggtgag tctgggcag gtgggcagga  12540 gaggtccccc caccactgct aaagggcaa ggttaggagt cccagatttg ggaggcctgg  12600
accaggtatc aagaggtctt tggaggagtt tggaggaaag ttgccactcc agattgacta  12660
cttagcaacc ccctgcatgg gcatggcttt ctaagcttca aagcaaggaa agagatcaca  12720
aatggaaaaa aaaacaaaa aacaaaaaaa cttgagattc aaccatataa acatgaaaac  12780
catctgtatt tcagaaagaa cctaaaaaag cattttaaa aaatcagcaa actgggagaa  12840
tatgtgcaag taccataaca gacaagaaga gtctaacatc tttcacatca gtgagctcat  12900
taacactaga ttccaatggt tagatgaggc agagtcacag gtaatttcaa ggtagctcat  12960
gaacaatgct cagcccagtt taaagcagta acacttactc cccagtgacg gcccattttc  13020
cactatggaa ttgctacagg gtggaggtgg gcagtgctgt ggggtgtgtt gtccggcctg  13080
```

-continued

```
cctcacccct ttccaactct cccctgcttc ccacgtcccc tctccccagc tcctgtactc   13140
gtcggtggag aacatccagc gcgtggctgc cggggtgctg tgtgagctgg cccaggacaa   13200
ggaggcggcc gacgccattg atgcagaggg ggcctcggcc ccactcatgg agttgctgca   13260
ctcccgcaac gagggcactg gtgagctggg ggagggcagg aggctgggtc ccactccccc   13320
agccacgatg gaggctggcc gacgtttaac ctggcttttc ctttcctctc tgctcagcca   13380
cctacgctgc tgccgtcctg ttccgcatct ccgaggacaa gaacccagac taccggaagc   13440
gcgtgtccgt ggagctcacc aactccctct tcaagcatga cccggctgcc tgggaggctg   13500
tgagtatcct aggttggacc gcagtagttg gttgtgcaag ttgggcactg cccatgggca   13560
acacttttgg gggtctccta ctactgtcaa cttcatagat ttttattttg taattggatc   13620
atttataaca attcctagca gatggaagta gtgggttgaa tcatatatcc acaaaatgcc   13680
aatttttatt ttgcccaaat gagtatacag tgtttgaggt gggggtgcct ttttgtaatt   13740
tgcgtggagg tgctggatag gctatgggcg gtctttttcca gggtggggca gtgccctgta   13800
cccattcttg agtcctctgc ctcctcccct gagctgctct agtccggcag gagtccctgc   13860
ttcatgagtg gggaaccctc ctccctgggg agtaccgagg acatgagtac atcagggcac   13920
tgggtgaccc catttcatca tcctctattc ctccaaggcc tctttgcttt tctccagccc   13980
cctcttttat ttatttattt attttttatat ttttttgagat ggagtcttgc tctgtcgcca   14040
ggctggagtc cagtggtgtg atcttggctc actgcaacct ccgcctcccg gtttcaagca   14100
attctcctgc ctcagccttc tgagtaactg ggactacagg tgcacgctac cacacccggc   14160 taattttttct atttttagta gagacgcggt ttcgccatgt tggccaggat gatctcgatt   14220
gtctcctgac cttgtgatcc gcccgccttg gcctcccaaa gtgctgggat tacaggcgtg   14280
agccagtgcg cccagcctat tttttatttt tttatgagac agagtctcac tcctgtcgcc   14340
caggctggag tgcaatggtg taatctcggc tcactgcatc ctctgcctcc ccattcaagc   14400
aattctcctg cctcagcctc ccgagtagct gggattacag gcctgcacca ccacgcccag   14460 ctaattttttt ttgtattttt agtagagaca gggtttcacc atgttggcca ggctggtctg   14520
gaactcctga cctcaagtga tccgcctgct gtctcccaga gtgctgggat tacaggcgtg   14580
agccacggca cccagcctgg ccccctcttt tagaagcatc tctccctgcc caccagctga   14640
gatccagctc ggagcctgca ttttcaaacc tcccctccat gtttctctct ccttttttcag   14700 gcccagagca tgattcccat caatgagccc tatggagatg gtaagtgtgt gccgggctct   14760
tcaggaccct ggagatcctg ggcggctgtg tgggtgtgtg ttaggggaca atattatgtc   14820
tccggggcca gaggaccagt ggcaactgct gtgtggcatc cacatgtacc ccagtctaga   14880
tgccctggtg tggggtctgg ggaagggggt caggcccacc aggggtgggc atgggtagag   14940
gaggcagctg aaggctgtgc agactgctcc ctgcagggta gcttgcagac cctaggaccg   15000
agccccactt tttgtcccca gacatggatg ccacctaccg ccccatgtac tccagcgatg   15060
tgccccttga cccgctggag atgcacatgg acatggatgg agactacccc atcgacacct   15120
acagcgacgg cctcaggccc ccgtacccca ctgcagacca catgctggcc taggcggcct   15180
ggccccagtg acgcccccct ctttgcaggc ttttcctcct ctctagaacc tccttctgtt   15240
ggaggccctc ccatctcccc gctgaaacct gcgctccttt tttgggggga tcctttgctg   15300
ctgagcttcc ccaagcacgg tgtgcccctgg cctgccttct tcttgtgtct ttggtgggga   15360
tggggaggcc tattcctgct ggcccccttct ggggtggtg ggcaggtgac acggagtggc   15420
ttgagcttct ggggatgcag gtccaccgag cccctgaccc ctgtctgtcc ccgctcccct   15480
```

-continued

```
aacaggtgcg gttcctcatc tgagaggctc tccgtgcagg cgatggggca agacagaaaa  15540
gtgcctgagc tggggaagcc ggggtgtaac ttcctgctgc accctgcgcc tccagaggtc  15600
ctccgtaggg tctttcttgg gatagtgttc tgctcctgct tttctgtcct gggcatgggt  15660
ccagggcctg acaccccctc cccgcccctg tggccctggc cactaaagct tcagactcaa  15720
gtacccattc tgttttcccc cagcaacgcc cctccaaacc tccagcctcc ctgtctccag  15780
ctgcctgggc ccggaagggc tttggttcct tctctgggtc tgattttctc actgaactcc  15840
accgaccaac tgccctaagc ccccagggcc tccagggccc aggttcgaga cccaaacccc  15900
caaaatccaa aacttctctt gaaaagttca gggaccgtcc aggggagatg gggaggagat  15960
atggagtgag tcacctgctc cagaagatgc cagcttctct ctccagggtg cttagttggc  16020
tttgcccacc cctcactccc cagggagctc cggggacagc ttcctcacac ccctgtccca  16080
cccacacagc tgccctagct gaccccgaga agtgctcttg gctgacccct ctggtgtgtg  16140
gtgaggggct ttctcttccc cttcctgttt cagacccccc catttcccgc acatggtgtg  16200
gggggctggg ggaggtccaa gcagagtgtt ttattattat cgctttatgt ttttggttat  16260
tggttttttt gtatagacca aagcaaagaa aataaaaata acacag          16306
```